US008852598B2

(12) United States Patent
Hooper

(10) Patent No.: US 8,852,598 B2
(45) Date of Patent: Oct. 7, 2014

(54) PUUMALA VIRUS FULL-LENGTH M SEGMENT-BASED DNA VACCINES

(75) Inventor: Jay Hooper, New Market, MD (US)

(73) Assignee: United States of America as represented by the Secretary of the Army

( * ) Notice: Subject to any disclaimer, the term of this patent is extended or adjusted under 35 U.S.C. 154(b) by 88 days.

(21) Appl. No.: 13/444,828

(22) Filed: Apr. 11, 2012

(65) Prior Publication Data

US 2013/0273170 A1    Oct. 17, 2013

Related U.S. Application Data

(62) Division of application No. 12/449,504, filed as application No. PCT/US2008/001847 on Feb. 12, 2008, now Pat. No. 8,183,358.

(60) Provisional application No. 60/901,414, filed on Feb. 12, 2007.

(51) Int. Cl.
*A61K 39/42* (2006.01)
*A61K 39/12* (2006.01)

(52) U.S. Cl.
USPC .................................. 424/159.1; 424/186.1

(58) Field of Classification Search
CPC ..................... C07K 16/08; C12N 2760/12111; C12N 2760/12121; C12N 2760/12122; C12N 2760/12171; A61K 2039/53; A61K 39/12
See application file for complete search history.

(56) References Cited

U.S. PATENT DOCUMENTS

| 5,837,441 A | 11/1998 | Hjelle | |
|---|---|---|---|
| 2002/0114818 A1* | 8/2002 | Schmaljohn et al. | ...... 424/278.1 |
| 2002/0197677 A1 | 12/2002 | Guttieri | |

OTHER PUBLICATIONS

Maes et al., Viral Immunology, 2008, 21(1):49-60.*
Maes et al., Expert Review Vaccines, 2009, 8(1):67-76.*
Lundkvist et al., "Characterization of puumala virus nucleocapsid protein . . . ", Virology 216, 1996, pp. 397-406.
McElroy et al., "Andes virus M genome segment is not sufficient . . . ", Virology 326 (2004), pp. 130-139.
Pertmer et al., "Gene gun-based nucleic acid immunization . . . ", Vaccine 1995, vol. 13, No. 15, pp. 1427-1430.
Rambukkana et al., "In situ behavior of human langerhans cells . . . ", Laboratory Investigation, vol. 73, No. 4, 1995, p. 521-531.
Robinson and Torres, "DNA Vaccines", seminars in Immunology, vol. 9, 1997, pp. 271-283.
Schmaljohn et al., "Antigenic subunits of hantaan virus expresses by baculovirus . . . ", J.Virology, Jul. 1990, vol. 64, No. 7, pp. 3162-3170.
Schmaljohn et al., "Preparation of canditate vaccinia-vectored vaccines . . . ", Vaccine, vol. 10, Issue 1, 1992, pp. 10-13.
Schmaljohn, C., "Molecular Biology of Hantaviruses", Chapter 3, Thje Bunyaviridae, ed. R.M. Elliott, Plenum Press, New York, 1996, pp. 63-90.
Schmaljohn and Hjelle, "Hantaviruses: a global disease problem", Emerging Infectious Diseases, vol. 3, No. 2, Apr.-Jun. 1997, pp. 95-104.
Schuurs and Van Weemen, "Review: Enzyme-Immunoassay", Clinica Chimica Acta, 81 (1977), pp. 1-40.
Song et al., "Preliminary human trial of inactivated golden hamster kidney cell (GHKC) . . . ", Vaccine, vol. 10, Issue 4, 1992, pp. 214-216.
Steele et al., "Cutaneous DNA Vaccination Against Ebola Virus by Particle Bombardment . . . ", Vet. Pathol. 38:203-215 (2001).
Ulrich et al., "Chimaeric HBV core particles carrying a defined segment of Puumala hantavirus nucleocapsid . . . ", Vaccine, vol. 16, No. 2/3, 1998, pp. 272-280.
Xiao et al., "Nucleotide and decuded amino acid sequences of the M and S genome . . . ", Virus Research 30 (1993) pp. 97-103.
Xu et al., "Immunity to hantavirus challenge in Meriones Unguiculatus induced by . . . ", Am. J. Trop. Med. Hyg. 47(4), 1992, pp. 397-404.
Yoshida et al., "Advantage of gene gun-mediated over intramuscular inoculation of plasmid DNA . . . ", Vaccine 18 (2000) pp. 1725-1729.
Yoshimatsu et al., "Protective immunity of Hantaa virus nucleocapsid and envelope . . . ", Arch Virol (1993), 130:365-376.
Draize et al., "Methods for the study of irritation and toxicity . . . ", paper from the Division of Pharmacology, Food and Drug Admin., Wash. D.C., 1944, pp. 377-390.
Haynes et al., "Accell particle-mediated DNA immunization elicits humoral . . . ", AIDS Research and Human Retroviruses, vol. 10, Suppl. 2, (1994), pp. S43-S45.
Lee et al., "Vaccines against hemorrhagic fever with renal syndrome", Factors in the Emergence and Control of Rodent-Borne Viral Diseases, 1999, pp. 147-156.
Stingl et al., "The Skin: initiation of target site of immune responses", Cancer Research, vol. 128, 1993, pp. 45-57.
Hooper, J. Powerpoint slideshow presented at XIII International Congress of Virology, Jul. 2005, slides 1-34, "Puumala virus M genone segment-based DNA Vaccine elicits . . . ".
Johsson et al., "Treatment of hantavirus pulmonary syndrome," Science Direct, Antiviral Research 78 (2008) pp. 162-169 (www.sciencedirect.com).
Kallio-Kokko et al.,"Human Immune Response to Puumala Virus Glycoproteins . . . " J. Medical Virology, 65:605-613 (2001).
Kennedy et al.,"Review: Protein—protein coupling reactions and the aplications of protein conjugate", Clinica Chimica Acta 70 (1976) pp. 1-31.
Khaw et al.,"Technetium-99m lageling of antibodies to cardiac myosin . . . ", Basic Sciences, J. Nucl. Med., vol. 23, No. 11, pp. 1011-1019 (1982).

(Continued)

*Primary Examiner* — Stacy B. Chen
(74) *Attorney, Agent, or Firm* — Elizabeth Arwine

(57) ABSTRACT

The invention contemplates a new synthetic, codon-optimized Puumala virus (PUUV) full-length M gene open reading frame (ORF) that encodes a unique consensus amino acid sequence. The PUUV ORF was cloned into a plasmid to form the first stable PUUV full-length M gene that elicits neutralizing antibodies. The gene can be engineered into a molecular vaccine system, and is useful to protect mammals against infection with Puumala virus.

7 Claims, 4 Drawing Sheets

(56) References Cited

OTHER PUBLICATIONS

Klinman et al., "Contribution of cells at the site of DNA vaccination to the generation . . . ", J. Immunology, 1998, 160:2388-2392.
Konishi et al., "Mice immunized with a subviral particle containing the Japanse encephalitis virus preM/M . . . ", Virology 188, 1992, pp. 714-720.
Labuda et al., "Importance of localized skin infection in tickborne . . . ", Virology 219, 1996, pp. 219-366.
Lee et al., "Field trial of an inactivated vaccine against hemorrhagic fever . . . ", Arch. Virol (1990) [suppl 1], pp. 35-47.
Qunying et al., "Immune responses to inactivated vaccine in people . . . ", J. Medical Virology, 49:333-335 (1996).
Eisenbraun et al., "Examination of parameters affecting the elicitation . . . ", DNA and Cell Biology, vol. 12, No. 9, 1993, pp. 791-797.
Fynan et al., "DNA vaccines: protective immunizations by parenteral . . . ", Proc. Natl. Acad. Sci. USA, vol. 90, Dec. 1993, pp. 11478-11482.
Fuller et al., "Preclinical and clinical progress of particle-mediated . . . ", Science Direct, Methods, 40 (2006), pp. 86-97 (www.sciencedirect.com).
Gregoriadis, G., "Review—Genetic Vaccines: Strategies for Optimization", Pharmaceutical Research, vol. 15, No. 5, 1998, pp. 661-670.
Gurunathan et al., "DNA vaccines: immunology, application and optimization", Annu.Rev.Immunol., 2000, 18:927-974.
Antibodies—A Laboratory Manual, ed. Harlow and Lane, Chapter 14 Immunoassays, pp. 555-612, Cold Spring Harbor Laboratory, 1988.

Hooper and Li, "Vaccines Against Hantaviruses", Current Topics in Microbiology and Immunology, vol. 256, Hantaviruses, ed.Schmaljohn & Nichol, Springer-Verlag 2001, pp. 171-191.
Hooper et al., "Rapid Communication—A lethal disease model for hantavirus . . . ", Virology 289, 2001, pp. 6-14.
Hooper et al., "Hantaan/Andes virus DNA vaccine elicits a broadly cross-reactive," Virology 347 (2006), pp. 208-216.
Hooper et al., "Immune serum produced by DNA vaccination . . . ", J. Virology, Feb. 2008, vol. 82, No. 3, pp. 1332-1338.
European Search Report dated May 3, 2010, issued in corresponding European Patent Application 08725473.6 (6 pages).
Database Uniprot online, accession No. P41266, Feb. 1, 1995 (2 pages).
Monteiro-Riviere et al., "The pig as a model for cutaneous pharmacology . . . ", Advances in Swine in Biomedical Res., ed. Tumbleson & Schook, Plenum Press, N.Y.,1996(425-458).
Arikawa et al., "Characterization of Hantaan Virus Envelope . . . ", J. gen. Viro. (1989), 70, 615-624.
Barry et al., "Biological features of genetic immunization," Vaccine, 1997, vol. 15, No. 8, pp. 788-791.
Bharadwaj et al., "Intramuscular inoculation of Sin Nombre . . . ", Vaccine 17 (1999) 2836-2843.
Bharadway et al., "Genetic vaccine protect against Sin Nombre . . . ", J. gen Vir. (2002) 83, 1745-1751.
Chu et al., "A vaccinia virus-vectored Hantaan virus vaccine . . . ", J. Virology, Oct. 1995, vol. 69, No. 10, 6417-6423.
Condon et al., "DNA-based immunization by in vivo transfection . . . ", Nature Medicine, vol. 2, No. 10 Oct. 1996, pp. 1122-1128.
Custer et al., "Active and passive vaccination against Hantavirus . . . ", J. Virology, Sep. 2003, vol. 77, No. 18, pp. 9894-9905.

* cited by examiner

Figures 3A (top) and 3B (bottom)

Neutralization of PUUV strain Sotkomo

Figure 4

PUUMALA VIRUS FULL-LENGTH M SEGMENT-BASED DNA VACCINES

This application is a divisional application of U.S. Ser. No. 12/449,504, filed Aug. 11, 2009. This application also claims priority from U.S. Provisional Application Ser. No. 60/901,414 filed Feb. 12, 2007, and PCT/US08/01847 (WO 2008/100508), filed Feb. 12, 2008. The entire contents of these documents are incorporated herein by reference.

BACKGROUND OF THE INVENTION

Currently, there are four known hantaviruses associated with hemorrhagic fever with renal syndrome (HFRS): Hantaan virus (HTNV), Dobrava-Belgrade virus (DOBV), Puumala virus (PUUV), and Seoul virus (SEOV). Because distinct hantaviruses are usually carried by only one principal rodent host species, their distribution is generally limited to the range of that host (reviewed in Schmaljohn and Hjelle, 1997, Emerg. Infect. Dis. 3, 95-104). HTNV, carried by Apodemus agrarius, is found in Asia; DOBV, carried by Apodemus flavicollis, and PUUV, carried by Clethrionomys glareolus, are found in Europe. SEOV is more widely disseminated than any other recognized hantaviruses because its host, the common urban rat (Rattus norvegicus), is found throughout the world.

Puumala virus (PUUV), genus Hantavirus, family Bunyaviridae, is responsible for the vast majority of hemorrhagic fever with renal syndrome (HFRS) cases in Scandinavia, Europe, and Western Russia. In addition to the HFRS associated hantaviruses, there are also several hantaviruses in North, Central, and South America (e.g. Andes virus [ANDV]) that cause a vascular-leak disease known as hantavirus pulmonary syndrome (HPS) (Jonsson, C. B., Hooper J, Mertz G. Treatment of hantavirus pulmonary syndrome. Antiviral Research 2007 Nov. 21 Epub ahead of print). Hantaviruses are carried by persistently infected rodents and transmission to humans occurs when persons are exposed to rodent secreta or excreta. This usually occurs when persons inhale aerosolized rodent excreta. There is no Food and Drug Administration (FDA) approved vaccine or specific drug to prevent or treat HFRS or HPS.

Viruses in the Hantavirus genus (family Bunyaviridae) are enveloped and contain a genome comprised of three single-stranded RNA segments designated large (L), medium (M), and small (S) based on size (reviewed in Schmaljohn, 1996, In The Bunyaviridae Ed. R. M. Elliott. New York, Plenum Press p. 63-90). The hantavirus L segment encodes the RNA dependent RNA polymerase, M encodes two envelope glycoproteins (G1 and G2, also known as $G_n$ and $G_c$), and S encodes the nucleocapsid protein (N).

A number of inactivated HFRS vaccines derived from cell culture or rodent brain were developed and tested in Asia (Lee et al., 1990, Arch. Virol., Suppl. 1, 35-47; Song et al., 1992, Vaccine 10, 214-216; Lu et al., 1996, J. Med. Virol. 49, 333-335). Drawbacks of these traditional killed-virus vaccines include a requirement for appropriate containment for the growth and manipulation of virus, and the necessity to ensure complete inactivation of infectivity without destroying epitopes on the virion important for protective immunity. In order to overcome these drawbacks, vaccine approaches involving recombinant DNA technology were developed including: vaccinia-vectored vaccines (Schmaljohn et al. 1990, J. Virol. 64, 3162-3170; Schmaljohn et al. 1992, Vaccine 10, 10-13; Xu et al. 1992, Am. J. Trop. Med. Hyg. 47, 397-404), protein subunit vaccines expressed in bacteria or insect cells (Schmaljohn et al. 1990, supra; Yoshimatsu et al., 1993, Arch. Virol. 130, 365-376; Lundkvist et al., 1996, Virology 216, 397-406), and a hepatitis core antigen-based recombinant vaccine (Ulrich et al., 1998, Vaccine 16, 272-280). For a review of hantavirus vaccine efforts see the review by Hooper and Li (Hooper and Li, 2001).

Vaccination with vaccinia recombinants expressing the M segment of either HTNV or SEOV elicited neutralizing antibodies and protected rodents against infection with both HTNV and SEOV, suggesting that an immune response to G1-G2 alone can confer protection (Schmaljohn et al. 1990, supra; Xu et al. 1992, supra; Chu et al. 1995, J. Virol. 69, 6417-6423). Similarly, vaccination with G1-G2 protein expressed in insect cells (baculovirus recombinant virus system) elicited neutralizing antibodies and protected hamsters from infection with HTNV (Schmaljohn et al. 1990, supra). In both the vaccinia and baculovirus systems, vaccination with G1-G2 provided more complete protection than G1 or G2 alone (Schmaljohn et al. 1990, supra). There are reports that candidate DNA vaccines comprised of around 500 nucleotide stretches of the Sin Nombre virus (SNV) M gene, or the full-length S gene, are immunogenic in mice (Bharadwaj, et al., 1999, Vaccine 17, 2836,43) and conferred some protection against infection with SNV in a deer mouse infection model (Bharadwaj, et al., 2002, J. Gen. Virol. 83, 1745-1751). The protection was surmised to be cell-mediated because there was no convincing evidence that these constructs elicited a neutralizing, or otherwise protective, antibody response. There have been several publications reporting the successful use of plasmid DNA vaccines containing the full-length M gene of SEOV, HTNV, ANDV, including the following reports:

1. Hooper, J. W., K. I. Kamrud, F. Elgh, D. Custer, and C. S. Schmaljohn (1999). DNA vaccination with hantavirus M segment elicits neutralizing antibodies and protects against Seoul virus infection. Virology, 255:269-278.
2. Hooper, J. W., D. Custer, E. Thompson, and C. S. Schmaljohn (2001). DNA Vaccination with the Hantaan virus M gene protects hamsters against three of four HFRS hantaviruses and elicits a high-titer neutralizing antibody response in rhesus monkeys. Journal of Virology 75:8469-8477.
3. Custer, D. M., E. Thompson, C. S. Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905.
4. Hooper, J. W., D. M. Custer, J. Smith, and Victoria Wahl-Jensen. Hantaan/Andes virus DNA vaccine elicits a broadly cross-reactive neutralizing antibody response in nonhuman primates (2006). Virology 347:208-216.

In all cases high titer neutralizing antibodies were detected in animals (including nonhuman primates) vaccinated with the full-length M gene DNA vaccines, and protection from infection was achieved in rodent models. Neutralizing antibody responses to G1-G2 in the aforementioned vaccine studies correlated with protection, suggesting that neutralizing antibodies not only play an important role in preventing hantavirus infection, but also might be sufficient to confer protection. Passive transfer of neutralizing monoclonal antibodies (MAbs) specific to either G1 or G2 protected hamsters against HTNV infection (Schmaljohn et al., 1990, supra; Arikawa et al., 1992, J. Gen. Virol. 70, 615-624), supporting the idea that neutralizing antibodies alone can confer protection. This is further supported by the finding that serum from nonhuman primates vaccinated using a gene gun with DNA vaccines containing the HTNV or ANDY full-length M genes protected hamsters from infection with HTNV or lethal disease caused by ANDV Custer, D. M., E. Thompson, C. S.

Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905). Similarly, sera from rabbits vaccinated with the ANDV M gene-based DNA vaccine using electroporation protected hamsters from a lethal challenge with ANDV (Hooper J. W., A. M. Ferro, and V. Wahl-Jensen. Immune Serum Produced by DNA Vaccination Protects Hamsters Against Lethal Respiratory Challenge with Andes Virus (2008). Journal of Virology 82:1332-1338.)

Like all members of the Bunyaviridae, PUUV are enveloped viruses with tri-segmented (S, M, and L), negative sense, RNA genomes. The M genome segment encodes the Gn and Gc surface glycoproteins. These proteins are the targets of neutralizing antibodies found in the convalescent serum of patients and infected animals. Hitherto, attempts to produce vaccines that produce neutralizing antibodies against PUUV have been unsuccessful.

Thus, there is currently no vaccine against hemorrhagic fever with renal syndrome (HFRS) caused by Puumala virus. Killed PUUV vaccine approaches have not resulted in a useful, licensed product anywhere in the world. Molecular vaccines using the PUUV N protein have been tested in animal infection models and there have been reports of protection in the absence of neutralizing antibodies. (See Hooper and Li, 2001) Whether an N protein-based PUUV will be effective in species other than mice remain unknown. Efforts to develop molecular vaccines that elicit neutralizing antibodies against PUUV have been ongoing for several years without success. Attempts to use HTNV, SEOV, and/or ANDV M gene-based DNA vaccines to produce antibodies to cross-neutralize PUUV have resulted in only very low levels of cross-neutralization, and no protection (see Hooper 2001 and Hooper 2006 referenced above). It is extremely difficult to construct a plasmid that is actually capable of eliciting good neutralizing antibody responses against PUUV, probably due at least in part to the instability of the full-length M gene in *E. coli* plasmid systems. This barrier has been overcome by the invention described herein.

In previous attempts, the inventor produced a version of a Puumala virus M gene-based DNA vaccine (designated pWRG/PUU-M-(x22), described below) that was capable of eliciting antibodies in monkeys after several vaccinations, but acceptable levels of neutralizing antibodies were not produced. Moreover, pWRG/PUU-M-(x22) was not immunogenic in hamsters. And finally, pWRG/PUU-M-(x22) was unstable during plasmid amplification in *E. coli* due to undefined properties of the M gene sequence.

The inventor is named as an inventor on other U.S. patents related to vaccines for hantaviruses and poxviruses, namely U.S. Pat. No. 6,451,309; U.S. Pat. No. 6,620,412; U.S. Pat. No. 6,562,376 and U.S. Pat. No. 7,217,812. The entire contents of these patents are incorporated herein by reference.

SUMMARY OF THE INVENTION

This invention contemplates a new recombinant PUUV full-length M segment [designated PUU-M(s2)], which is useful to elicit neutralizing antibodies against PUUV. Key to the invention is a novel synthetic, codon-optimized Puumala virus full-length M gene open reading frame (ORF) that has a unique consensus amino acid sequence including five amino acid alterations relative to the ORF in the M gene contained in a plasmid designated pWRG/PUU-M-(x22), which was also created by the inventor and is described in detail below. In addition, as described in more detail below, it is very preferred that the DNA sequence of the Puumala virus M gene ORF be altered in such a way as to eliminate sequences that destabilize the plasmid in *E. coli*. The ORF nucleic acid sequence was changed without altering the coded amino acid sequence. This was accomplished by codon optimizing the ORF. The process of codon optimization not only changed the nucleic sequence, but also it was intended to allow more efficient codon usage and increased stability of the mRNA produced by the plasmid. An algorithm called GeneOptimizer (patent pending), owned by GeneArt was used to allow more efficient codon usage and stabilization of the mRNA. It is noted that, while the ORF was codon optimized, the flanking sequence was unchanged.

This synthetic M gene can be, and has been, engineered into molecular vaccine systems, whether that be a DNA vaccine plasmid (i.e, pWRG/PUU-M(s2)), or virus-vectored vaccine. The preferred DNA plasmid containing this sequence is designated pWRG/PUU-M(s2), and its DNA sequence is described in detail below. In contrast to its ancestor pWRG/PUU-M-(x22), pWRG/PUU-M(s2) is capable of eliciting good neutralizing antibody responses against Puumala virus. In fact, pWRG/PUU-M(s2), as a DNA vaccine delivered by gene gun, is the first molecular vaccine of any kind that has elicited convincing levels of neutralizing antibodies against Puumala virus in animals, including non-human primates.

The development of this novel PUUV full-length M segment and its used as a molecular vaccine can be summarized as follows. In earlier attempts, the inventor cloned an intact ORF from a known Puumala virus, strain K27, M gene, and successfully detected expression of both the G1 and G2 glycoproteins in vitro. The plasmid was designated pWRG/PUU-M-(x22) by the inventor, and remained proprietary and unpublished. pWRG/PUU-M-(x22) was constructed by reverse transcriptase of viral RNA, polymerase chain reaction amplification of cDNA, and standard cloning techniques. The DNA sequence of the M gene in pWRG/PUU-M-(x22) is indicated below as SEQ ID NO:4—it was almost identical to the published sequence of the K27 M gene (GeneBank accession No. L08754) that was previously determined by sequencing partial M gene clones, aligning sequences, and constructing the full-length sequence in slico (Xiao S Y, Spik K W, Li D, and Schmaljohn C S 1993).

```
SEQ ID NO: 4
-- PUU-M(x22) Open Reading Frame.SEQ ID NO: 5 shows the
amino acid sequence of the M gene peptide product, and the
five amino acids that were changed in PUU-M(s2)are boxed.

------1 ATG GGGA GAA CTT AGT CCA GTT TGT CTG TAT CTG CTT
CTC CAG GGT CTA TTA CTA TGT AAT ACA GGG GCT GCC AGA 75
   1M  G    E   L   S   P   V   C   L   Y   L   L
  L   Q   G   L   L   L   C   N   T
  G   A   A   R 25

76 AAC CTT AAT GAG CTT AAA ATG GAA TGT CCA CAT ACT
   ATT AGA TTA GGG CAG GGT CTT GTT GTC GGT TCA GTA GAA 150
```

-continued
```
    26 N L N E L K M E C P H T I R L G Q G L V V
G S V E 50

151 TTG CCA TCT CTT CCA ATA CAG CAG GTC GAG ACA CTA
AAG CTG GAG AGT TCT TGT AAT TTT GAT CTA CAT ACC AGT 225
    51 L P S L P I Q Q V E T L K L E S S C N F D L
H T S 75

226 ACA GCA GGA CAA CAA TCA TTC ACA AAA TGG ACA TGG
GAA ATT AAA GGT GAT CTT GCA GAG AAC ACA CAG GCA TCA
300
    76 T A G Q Q S F T K W T W E I K G D L A E N
T Q A S 100

301 TCA ACA AGT TTT CAA ACA AAA AGC AGT GAA GTG AAT
TTG AGA GGA TTA TGT TTG ATC CCT ACT TTA GTG GTT GAA 375
   101 S T S F Q T K S S E V N L R G L C L I P T
L V V E 125

376 ACA GCA GCA AGA ATG CGA AAA ACA ATA GCA TGT TAT
GAC CTG TCA TGC AAT CAA ACA GTG TGT CAG CCT ACT GTC 450
   126 T A A R M R K T I A C Y D L S C N Q T V
C Q P T V 150

451 TAT TTA ATG GGA CCT ATC CAG ACT TGT ATA ACA ACT
AAA AGT TGT CTC TTG AGT TTA GGT GAT CAA AGG ATT CAA 525
   151 Y L M G P I Q T C I T T K S C L L S L G D
Q R I Q 175

526 GTA AAT TAT GAA AAA ACA TAC TGT GTT TCT GGG CAG
CTT GTT GAA GGT ATC TGT TTT AAT CCA ATA CAT ACA ATG 600
   176 V N Y E K T Y C V S G Q L V E G I C F N P
I H T M 200

601 GCA CTC TCT CAA CCT AGT TAT ACA TAT GAT ATA ATG
ACC ATG ATG GTT CGC TGT TTC TTG GTA ATA AAG AAA GTG 675
   201 A L S Q P S ☒ T Y D I M T M M V R C F L
V I K K V 225

676 ACT TCT GGT GAC AGT ATG AAG ATT GAA AAG AAC TTT
GAG ACT CTT GTT CAA AAA AAT GGC TGC ACA GCT AAT AAC 750
   226 T S G D S M K I E K N F E T L V Q K N G C
T A N N 250

751 TTC CAA GGG TAT TAT ATC TGT CTT ATA GGG AGT AGT
TCA GAG CCC TTA TAT GTT CCA GCA TTA GAT GAT TAT CGT 825
   251 F Q G Y Y I C L I G S S S E P L Y V P A L
D D Y R 275

826 TCA GCT GAA GTT CTT TCA AGG ATG GCA TTT GCA CCA
CAT GGT GAA GAT CAT GAT ATT GAG AAA AAT GCA GTG AGT
900
   276 S A E V L S R M A F A P H G E D H D I E K
N A V S 300

901 GCA ATG CGT ATT GCT GGA AAG GTG ACA GGA AAG GCG
CCA TCA ACA GAA TCA TCA GAT ACA GTA CAG GGG ATT GCA
975
   301 A M R I A G K V T G K A P S T E S S D T V
Q G I A 325

976 TTT TCA GGT AGT CCT CTT TAT ACA TCT ACT GGT GTC TTG
ACA TCA AAA GAT GAT CCT GTC TAC ATT TGG GCT CCT 1050
   326 F S G S P L Y T S T G V L T S K D D P V Y
I W A P 350

1051 GGA ATC ATA ATG GAA GGA AAC CAT TCT ATT TGT GAA
AAG AAG ACC TTA CCC CTT ACA TGG ACT GGT TTT ATT TCA 1125
   351 G I I M E G N H S I C E K K T L P L T W T
G F I S 375

1126 TTG CCT GGA GAG ATT GAA AAA ACA ACA CAA TGT ACA
GTA TTT TGT ACA TTG GCT GGA CCA GGT GCA GAT TGT GAA
1200
   376 L P G E I E K T T Q C T V F C T L A G P G
A D C E 400

1200 GCT TAC TCT GAA ACA GGC ATC TTC AAC ATA AGT TCA
CCT ACT TGC TTA ATA AAT CGT GTC CAG AGA TTC CGT GGT 1275
   401 A Y S E T G I F N I S S P T C L I N R V Q R
F R G 425
```

-continued

```
1276 TCA GAA CAG CAA ATA AAG TTT GTG TGC CAG AGA GTG
GAC ATG GAT ATC ACT GTT TAC TGT AAT GGG ACG AAG AAA
1350
   426 S E Q Q I K F V C Q R V D M D I T V Y C N
G  K K 450
```

```
1351 GTC ATT CTC ACC AAG ACC CTA GTT ATT GGA CAA TGC
ATT TAT ACT TTT ACT AGT ATT TTC TCT CTA ATC CCT GGT 1425
   451 V I L T K T L V I G Q C I Y T F T S I F S L
I P G 475

1426 GTT GCA CAT TCC CTT GCT GTT GAA TTA TGT GTA CCT
GGT CTT CAT GGT CGG GCA ACT ATG CTA TTA CTA ACA
1500
   476 V A H S L A V E L C V P G L H G  A T M
L L L L T 500
```

```
1501 TTT TGT TTT GGC TGG GTC TTA ATA CCA ACT ATA ACA
ATG ATC CTG CTA AAG ATA TTG ATT GCA TTC GCA TAC TTA 1575
   501 F C F G W V L I P T I T M I L L K I L I A F
A Y L 525

1576 TGT TCT AAA TAT AAC ACA GAT TCG AAA TTC AGG ATC
TTG ATT GAG AAA GTG AAA AGA GAG TAC CAG AAA ACA ATG
1650
   526 C S K Y N T D S K F R I L I E K V K R E Y
Q K T M 550

1651 GGT TCA ATG GTT TGT GAA GTG TGT CAG TAT GAA TGT
GAG ACT GCA AAA GAA CTG GAG TCA CAT AGA AAG AGT TGT
1725
   551 G S M V C E V C Q Y E C E T A K E L E S
H R K S C 575

1726 TCC ATT GGT TCA TGC CCT TAT TGT CTC AAT CCA TCT
GAG GCA ACA ACA TCT GCC CTT CAG GCT CAT TTT AAA GTG
1800
   576 S I G S C P Y C L N P S E A T T S A L Q A
H F K V 600

1801 TGT AAG CTC ACA TCA CGG TTT CAG GAG AAT TTA AGA
AAG TCA TTA ACG GTA TAT GAG CCT ATG CAA GGG TGC TAC
1875
   601 C K L T S R F Q E N L R K S L T V Y E P M
Q G C Y 625

1876 CGG ACT TTA TCC CTC TTT AGA TAT AGG AGT CGG TTC
TTT GTG GGT CTA GTC TGG TGC GTG TTA TTG GTT CTA GAG 1950
   626 R T L S L F R Y R S R F F V G L V W C V L
L V L E 650

1951 TTA ATT GTA TGG GCT GCC AGT GCT GAA ACA CAA AAT
TTA AAT GCA GGT TGG ACA GAC ACA GCA CAT GGA TCT GGA
2025
   651 L I V W A A S A E T Q N L N A G W T D T
A H G S G 675

2026 ATT ATA CCT ATG AAA ACT GAT CTG GAA TTA GAC TTC
TCT CTT CCG TCA TCA GCA AGC TAT ACA TAT AGG AGA CAG
2100
   676 I I P M K T D L E L D F S L P S S A S Y T
Y R R Q 700

2101 CTA CAA AAC CCA GCA AAC GAA CAA GAG AAA ATC CCA
TTT CAT CTG CAG TTA AGC AAA CAA GTG ATT CAT GCA GAG
2175
 701 L Q N P A N E Q E K I P F H L Q L S K Q V
I H A E 725

2176 ATC CAG CAT TTA GGT CAT TGG ATG GAT GCT ACA TTT
AAT CTT AAA ACT GCA TTT CAC TGC TAT GGC TCA TGT GAG
2250
   726 I Q H L G H W M D A T F N L K T A F H C
Y G S C E 750

2251 AAG TAT GCT TAT CCT TGG CAG ACA GCA GGT TGT TTC
ATA GAA AAA GAT TAT GAA TAT GAG ACT GGT TGG GGT TGT
2325
```

-continued
```
  751 K Y A Y P W Q T A G C F I E K D Y E Y E
T G W G C 775

2326 AAT CCA CCT GAT TGC CCA GGG GTA GGG ACA GGC TGT
ACT GCT TGT GGG GTA TAC CTT GAT AAA TTA AAA TCA GTT
2400
  776 N P P D C P G V G T G C T A C G V Y L D
K L K S V 800

2401 GGA AAG GTT TTC AAA ATT GTG TCC TTA AGA TAC ACA
AGG AAA GTA TGC ATT CAG TTG GGC ACA GAA CAA ACA TGT
2475
  801 G K V F K I V S L R Y T R K V C I Q L G T
E Q T C 825

2476 AAG ACT GTT GAT AGT AAT GAC TGT CTC ATT ACC ACT
TCA GTT AAA GTG TGC TTG ATA GGG ACC ATA TCA AAA TTC
2550
  826 K T V K S N D C L I T T S V K V C L I G T
I S K F 850

2551 CAA CCA TCT GAC ACT TTG CTA TTT CTA GGT CCA CTA
CAG CAG GGT GGT CTG ATA TTT AAA CAA TGG TGC ACT ACA
2625
  851 Q P S D T L L F L G P L Q Q G G L I F K Q
W C T T 875

2626 ACA TGC CAG TTT GGC GAT CCC GGG GAC ATA ATG AGC
ACA CCT ACA GGC ATG AAG TGC CCA GAA TTA AAT GGT TCT
2700
  876 T C Q F G D P G D I M S T P T G M K C P E
L N G S 900
```

(Note: protein line shows "T C Q F G D P G D D I M S T P T G M K C P E")

```
 2701 TTT AGA AAG AAA TGT GCA TTT GCA ACA ACT CCA GTT
TGC CAG TTT GAT GGA AAT ACA ATT TCA GGC TAT AAG AGG
2775
  901 F R K K C A F A T T P V C Q F D G N T I S
G Y K R 925

2776 ATG ATT GCC ACA AAG GAT TCA TTT CAA TCT TTC AAT
GTG ACA GAA CCC CAT ATT TCT ACA AGT GCA CTT GAA TGG
2850
  926 M I A T K D S F Q S F N V T E P H I S Y S
A L E W 950

2851 ATT GAT CCT GAC AGC TCA CTT AGG GAC CAT ATT AAT
GAT ATT GTG AGT CGT GAT CTA TCC TTC CGA GAC CTA AGT
2925
  951 I D P D S S L R D H I N V I V S R D L S R
D L S 975

2926 GAA ACA CCA TGT CAA ATT GAT TTA GCA ACA GCC TCT
ATA GAT GGA GCA TGG GGT TCA GGA GTT GGT TTT AAT CTG
3000
  976 E T P C Q I D L A T A S I D G A Q G S G V
G F N L 1000

3001 GTT TGT ACT GTT AGT TTA ACA GAA TGT TCT GCA TTT
CTG ACA TCA ATC AAG GCC TGT GAT GCT GCA ATG TGT TAT
3075
 1001 V C T V S L T E C S A F L T S I K A C D A
A M C Y 1025

3076 GGG TCC ACC ACA GCC AAT CTA GTT CGA GGG CAA AAT
ACC ATT CAT ATC GTC GGT AAG GGT GGG CAT TCT GGT TCA
3150
 1026 G S T T A N L V R G Q N T I H I V G K G G
H S G S 1050

3151 AAA TTT ATG TGT TGT CAT GAC ACA AAA TGT TCT AGC
ACC GGT CTA GTT GCA GCT GCA CCA CAC TTA GAT CGT GTG
3225
 1051 K F M C C H D T K C S S T G L V A A A P
H L D R V 1075
```

```
3226 ACA GGA TAC AAT CAG GCT GAT AGT GAC AAA ATC TTT
GAT GAT GGG GCA CCA GAA TGT GGT ATG TTA TGT TGG TTT
3300
  1076 T G Y N Q A D S D K I F D D G A P E C G
M C W F 1100

3301 AAA AAA TCA GGT GAA TGG ATT CTT GGG GTT TTG AAC
GGG AAT TGG ATG GTT GTT GCT GTA CTG GTA GTA TTA CTG
3375
 1101 K K S G E W I L G V L N G N W M V V A V
L V V L L 1125

3376 ATC TTG TCC ATA CTC TTA TTC ACA TTA TGT TGT CCT CGT
AGA CCT AGT TAC AGG AAA GAA CAT AAG CCC TAA 3447
 1126 I L S I L L F T L C C P R R P S Y R K E H
K P * 1149
```

It was found that pWRG/PUU-M-(x22) was capable of eliciting antibodies in monkeys after several vaccinations using a gene gun, but good neutralizing antibodies were not produced. In addition, the plasmid pWRG/PUU-M-(x22) delivered by gene gun was not immunogenic in hamsters (i.e., no antibodies detected and no protection from infection following challenge). Thus, there were two main immunogenic issues presented by pWRG/PUU-M-(x22): (1) the inventor could not detect neutralizing antibodies in hamsters vaccinated with pWRG/PUU-M-(x22), and (2) the antibodies elicited in nonhuman primates were not neutralizing, or poorly neutralizing. Moreover, pWRG/PUU-M-(x22) was unstable due to undefined properties of the M gene sequence—and consequently appeared to be of minimal use.

Using pWRG/PUU-M-(x22), the inventor constructed another plasmid designated pWRG/PUU-M (s1), which contained the same M gene open reading frame but was codon optimized. As a result of the nucleic acid changes made during codon optimization, pWRG/PUU-M (s1) was a very stable plasmid and large amounts of DNA have been made without difficulty.

However, when pWRG/PUU-M (s1) was tested, it failed to elicit good neutralizing antibody levels in nonhuman primates vaccinated with a gene gun.

The goal was to develop a Puumala virus M gene-based vaccine that could elicit neutralizing antibodies in small animal models and nonhuman primates (and ultimately in humans), while maintaining stability of the ORF within the bacterial plasmid. Of course, such a vaccine would be useful against Puumala virus infection in humans. The inventor discovered that there were several nucleotide differences between the ORF in pWRG/PUU-M-(x22) and several of the partial clones they had obtained during earlier attempts to clone the intact full-length M gene ORF. Differences in their cloned sequence and the published Puumala virus strain K27 and other Russian strains were also detected. Five of these nucleotide changes resulted in amino acid substitutions that were unique to the M gene in pWRG/PUU-M-(x22) and therefore were suspected to be possible cloning artifacts. Based on this information, the inventor tested the hypothesis that one or more of these five amino acid changes altered the immunogenicity of the glycoproteins—these five amino acids were unique to the PUU-M(x22) clone; all of the other ~1149 amino acids were shared by at least 1 strain of PUUV. A consensus amino acid, codon-optimized version of pWRG/PUU-M-(x22) was synthesized, designated pWRG/PUU-M (s2). (By "consensus" it is meant that when multiple clones, and published sequences were aligned, aberrant unique changes could be identified and changed to an amino acid shared by two or more independent sequences.) At the nucleic acid level, this plasmid was identical to pWRG/PUU-M(s1), except at the positions resulting in the 5 amino acid changes (relative to the amino acid sequence of the M gene in pWRG/PUU-M-(x22) and pWRG/PUU-M(s1)). pWRG/PUU-M(s1) and pWRG/PUU-M(s2) were produced at the same time—the inventor hypothesized that the 5 amino acid corrections would solve the problem. Both clones were synthesized at the same time. pWRG/PUU-M(s1) was included because it was desirable to have a control, and to test if the codon optimization alone was sufficient. As it turned out, the codon optimization alone wasn't sufficient.

Specifically, the amino acids (aa) that were altered in pWRG/PUU-M-(x22) to create pWRG/PUU-M(s2) are as follows (where the first letter is the aa designation in x22, followed by the aa number, followed by the aa designation in s2):

Y207H,
T448M,
R492W,
R972Q, and
L1097S.

The corresponding alterations in the DNA sequence of the Puumala virus M-gene open reading frame that result in the amino acid changes are (where the first codon is from x22, followed by the codon from s2, followed by the aa number):

tat to cac at amino acid number 207;
act to atg at amino acid number 448;
cgg to tgg at amino acid number 492;
cga to cag at amino acid number 972; and
tta to agt at amino acid number 1097.

The nucleotide one letter code is defined as the following: a=adenine, t=thymine, c=cytosine, and g=guanine.

The amino acid one letter code is defined as the following: A=Alanine (Ala), I=Isoleucine (Ile), L=Leucine (Leu), M=Methionine (Met), F=Phenylalanine (Phe), P=Proline (Pro), W=Tryptophan (Trp), V=Valine (Val), N=Asparagine (Asn), C=Cysteine (Cys), Q=Glutamine (Q), G=Glycine (Gly), S=Serine (Ser), T=Threonine (Thr), Y=Tyrosine (Tyr), R=Arginine (Arg), H=Histidine (H is), K=Lysine (Lys), D=Aspartic acid (Asp), and E=Glutamic acid (Glu).

The pWRG/PUU-M(s2) plasmid DNA has been produced successfully and sequence data indicate the plasmid is stable and can be produced to high levels efficiently.

As would be understood by someone having skill in this art, this invention covers sequences that are not necessarily physically derived from the nucleotide sequence itself, but may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use.

It is also understood in the art that certain changes to the nucleotide sequence employed in a genetic construct have little or no bearing on the proteins encoded by the construct, for example due to the degeneracy of the genetic code. Such changes result either from silent point mutations or point mutations that encode different amino acids that do not appreciably alter the behavior of the encoded protein. It is understood that portions of the coding region can be eliminated without affecting the ability of the construct to achieve the desired effect, namely induction of a protective immune response against Puumala virus. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the M segment of Puumala virus are equivalents within the scope of the present invention.

The DNA encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector, such as an adenovirus, alphavirus replicon or vescicular stomatitis virus. Individual expression vectors capable of expressing the genetic material can be produced using standard recombinant techniques.

Experimentation revealed that pWRG/PUU-M(s2), but not pWRG/PUU-M (s1), elicited good neutralizing antibody levels in nonhuman primates vaccinated with a gene gun. pWRG/PUU-M(s2) also elicited neutralizing antibodies in hamsters vaccinated with a gene gun. Vaccinated hamsters were protected against challenge with PUUV, strain K27. Cross-neutralization plaque reduction neutralization tests indicate the antibodies produced in nonhuman primates vaccinated with pWRG/PUU-M(s2) using a gene gun cross neutralize the prototype Scandinavian strain of PUUV, strain Sotkamo.

Thus, the inventor have created a novel, synthetic codon optimized Puumala virus full-length M gene that is stably maintained in a DNA vaccine plasmid, and elicits good neutralizing antibodies in animal models. Heretofore, there was no full length PUUV M gene clone stably inserted iton an expression plasmid, that could be successfully expressed. The discovery that pWRG/PUU-M-(x22) could elicit antibodies but a poor neutralizing response even after five vaccinations is what instigated the thought process leading to the re-engineering of the construct. The idea was that the G1-G2 oligomers produced from pWRG/PUU-M-(x22) were not folding into the precise conformation required for presentation of neutralizing epitopes to the immune system. Careful examination of the amino acid sequence revealed 5 amino acid residues, of the more than 1000, were unique to the pWRG/PUU-M-(x22) plasmid and therefore could be cloning artifacts. Several other amino acids differed from the amino acids sequences of PUUV strain K27, however, these amino acid differences were shared by other strains of PUUV, or in other independent partial clones the inventor had generated during the effort to clone the full-length gene. Only five were unique to pWRG/PUU-M-(x22), and it was those five that were changed. The choice of what amino acid to substitute was made by looking at the consensus sequence of the published PUUV M genes and the inventor's other independent partial clones.

Thus, one point of novelty of the invention is that it elicits Puumala virus neutralizing antibodies. To the best of the inventor's knowledge, there is no other molecular vaccine that elicits antibodies that directly neutralize Puumala virus. It is noted that there is one publication in which a formalin-inactivated suckling-hamster brain-derived alumn-adjuvanted PUUV vaccine was reported to elicit antibodies that neutralized PUUV (Ho-Wang Lee, et al., Vaccines against hemorrhagic fever with renal syndrome. In, Factors in the Emergence and Control of Rodent-borne Viral Diseases (Hanaviral and Arenal Diseases). J. F. Saluzzo, B. Dodet eds. 1999 Editions scientifiques et medicales Elsevier SAS). However, the subject vaccine is advantageous because (1) it does not require the use of live Puumala virus, which is a BSL-3 agent; (2) it does not require growing virus in rodent brains; (3) it does not require extensive testing to ensure inactivation; and (4) it does not require formulation with alumn adjuvant. The fact that our vaccine is a gene-based molecular vaccine indicates that the G1 and G2 proteins will be produced within the vaccines cells and therefore will be presented to the immune system in a manor that more closely resembles an infection than the injection of inactivated virus. The subject construct can also be used for the production of pseudotypes—which cannot be done with a killed virus vaccine.

In addition, there are no other DNA vaccines or other expression vectors that express full-length, functional (elicit neutralizing antibodies) Puumala virus G1 and G2 glycoproteins. There is one report of a Alphavirus-replicon vectored construction that expressed Puumala virus G1 and G2, but those proteins were never shown to be functional or to elicit antibody responses in vaccinated animals. (Kallio-Kokko H, et al. (2001) Human immune response to Puumala virus glycoprotein and nucleocapsid protein expressed in mammalian cells. J Med. Virol. 65:605-13.)

Thus, in a first embodiment the invention entails an isolated nucleic acid sequence of the Puumala virus full-length M segment open reading frame, which is (1) a codon-optimized version of the open reading frame in a plasmid containing a full-length M gene, pWRG/PUU-M-(x22), and (2) altered at five codons in its DNA sequence such that, based on the M gene in pWRG/PUU-M-(x22), the following codons are changed tat in M(x22) to cac M(s2) at amino acid number 207, to change amino acid Y to amino acid H;

act M(x22) to atg M(s2) at amino acid number 448, to change amino acid T to amino acid M;

cgg M(x22) to tgg M(s2) at amino acid number 492, to change amino acid R to amino acid W;

cga M(x22) to cag M(s2) at amino acid number 972, to change amino acid R to amino acid Q and tta M(x22) to agt M(s2) at amino acid number 1097, to change amino acid L to amino acid S.

Thus, using pWRG/PUU-M-(x22) as a basis, five suspect amino acids were converted to those found in other published sequences, or sequence obtained during construction of pWRG/PUU-M-(x22). The plasmid containing the synthetic gene is designated pWRG/PUU-M(s2). The isolated nucleic acid sequence of the Puumala virus full-length M segment open reading frame of this invention is set forth below, and referred to hereafter as SEQ ID NO:1.

```
SEQ ID NO: 1
- synthetic Puumala virus full-length
M segment ORF
ATGGGCGAGCTGTCCCCTGTGTGCCTGTACCTGCTGCTGCAGGGCCTGCT

GCTGTGTAACACCGGAGCCGCCAGGAACCTGAACGAGCTGAAGATGGAGT

GCCCCCACACCATCAGACTGGGCCAGGGCCTGGTGGTGGGCAGCGTGGAG

CTGCCCAGCCTGCCCATCCAGCAGGTGGAGACCCTGAAGCTGGAGAGCAG
```

```
CTGTAACTTCGACCTGCACACCAGCACAGCCGGCCAGCAGAGCTTCACCA
AGTGGACCTGGGAGATCAAGGGCGACCTGGCCGAGAACACCCAGGCCAGC
AGCACCAGCTTCCAGACCAAGAGCAGCGAGGTGAACCTGAGAGGCCTGTG
CCTGATCCCCACACTGGTGGTGGAGACCGCCGCCAGAATGAGAAAGACCA
TCGCCTGCTACGACCTGAGCTGTAACCAGACCGTGTGTCAGCCTACCGTG
TACCTGATGGGCCCTATCCAGACCTGTATCACCACCAAGAGCTGCCTGCT
GTCCCTGGGCGATCAGAGAATCCAGGTGAACTACGAGAAAACCTACTGTG
TGAGCGGCCAGCTGGTGGAGGGCATCTGCTTCAACCCCATCCACACCATG
GCCCTGAGCCAGCCTAGCCACACCTACGACATCATGACCATGATGGTGAG
ATGCTTTCTGGTGATCAAGAAGGTGACCAGCGGCGACAGCATGAAGATCG
AGAAGAACTTCGAGACCCTGGTGCAGAAGAATGGCTGTACCGCCAACAAC
TTCCAGGGCTACTACATCTGCCTGATCGGCAGCAGCAGCGAGCCCCTGTA
CGTGCCCGCCCTGGACGACTACAGAAGCGCCGAGGTGCTGTCCAGAATGG
CCTTCGCCCCCCACGGCGAGGACCACGACATCGAGAAAAACGCCGTGTCC
GCCATGAGAATCGCCGGCAAGGTGACCGGCAAGGCCCCCAGCACCGAGTC
CAGCGACACCGTGCAGGGCATCGCCTTCAGCGGCAGCCCCCTGTACACCT
CCACCGGCGTGCTGACCAGCAAGGACGACCCCGTGTACATCTGGGCCCCT
GGCATCATCATGGAGGGCAACCACAGCATCTGTGAGAAGAAAACCCTGCC
CCTGACCTGGACCGGCTTCATCAGCCTGCCCGGCGAGATCGAGAAAACCA
CCCAGTGTACCGTGTTCTGTACCCTGGCCGGACCTGGCGCCGACTGTGAG
GCCTACAGCGAGACCGGCATCTTCAACATCAGCAGCCCCACCTGCCTGAT
CAACCGGGTGCAGAGGTTCAGAGGCAGCGAGCAGATCAAGTTTGTGT
GCCAGCGGGTGGACATGGACATCACCGTGTACTGTAACGGCATGAAGAAG
GTGATCCTGACCAAGACACTGGTGATCGGCCAGTGTATCTACACCTTCAC
CAGCATCTTCTCCCTGATCCCCGGCGTGGCCCACAGCCTGGCCGTGGAGC
TGTGTGTGCCCGGCCTGCACGGCTGGGCCACCATGCTGCTGCTGCTGACC
TTCTGCTTCGGCTGGGTGCTGATCCCTACCATCACCATGATCCTGCTGAA
GATCCTGATCGCCTTCGCCTACCTGTGCTCCAAGTACAACACCGACAGCA
AGTTCAGAATCCTGATCGAGAAAGTGAAGCGGGAGTACCAGAAAACCATG
GGCAGCATGGTGTGTGAAGTGTGCCAGTACGAGTGTGAGACCGCCAAGGA
GCTGGAGTCCCACAGAAAGAGCTGCTCCATCGGCAGCTGCCCCTACTGCC
TGAACCCCAGCGAGGCCACCACCTCCGCCCTGCAGGCCCACTTCAAAGTG
TGTAAGCTGACCAGCCGGTTCCAGGAGAACCTGAGGAAGTCCCTGACCGT
GTACGAGCCCATGCAGGGCTGCTACAGAACCCTGAGCCTGTTCCGGTACA
GGAGCCGGTTCTTTGTGGGCCTGGTGTGGTGTGTGCTGCTGGTGCTGGAG
CTGATTGTGTGGGCCGCCAGCGCCGAGACCCAGAACCTGAATGCCGGCTG
GACCGACACCGCCCACGGCAGCGGCATCATCCCCATGAAAACCGACCTGG
AGCTGGACTTCAGCCTGCCTAGCAGCGCCTCCTACACCTACAGGCGGCAG
CTGCAGAATCCTGCCAACGAGCAGGAGAAGATCCCCTTCCACCTGCAGCT
GTCCAAGCAGGTGATCCACGCCGAGATTCAGCACCTGGGCCACTGGATGG
ACGCCACCTTCAACCTGAAAACCGCCTTCCACTGCTACGGCAGCTGTGAG
AAGTACGCCTACCCTTGGCAGACCGCCGGCTGCTTCATCGAGAAGGACTA
CGAGTACGAGACCGGCTGGGGCTGTAATCCTCCTGATTGCCCCGGAGTGG
GCACCGGCTGTACTGCATGTGGCGTGTACCTGGACAAGCTGAAGTCTGTG
GGCAAGGTGTTCAAGATCGTGTCCCTGAGGTACACCCGGAAAGTGTGTAT
CCAGCTGGGCACCGAGCAGACCTGTAAGACCGTGGACAGCAACGATTGCC
TGATCACAACCAGCGTGAAAGTGTGTCTGATCGGCACCATCAGCAAGTTC
CAGCCCAGCGATACCCTGCTGTTTCTGGGCCCCCTGCAGCAGGGCGGCCT
GATCTTCAAGCAGTGGTGTACCACCACCTGCCAGTTCGGCGATCCCGGCG
ATATCATGAGCACCCCCACCGGCATGAAGTGCCCTGAGCTGAACGGCAGC
TTCCGGAAGAAGTGTGCCTTCGCCACCACCCCTGTGTGTCAGTTCGACGG
CAACACCATCAGCGGCTACAAGCGGATGATCGCCACCAAGGACAGCTTCC
AGTCCTTCAACGTGACCGAGCCCCACATCAGCACCAGCGCCCTGGAGTGG
ATCGATCCCGACAGCAGCCTGAGGGACCACATCAACGTGATCGTGTCCAG
GGACCTGAGCTTCCAGGACCTGAGCGAGACCCCCTGCCAGATCGACCTGG
CCACCGCCAGCATCGATGGCGCCTGGGGCAGCGGAGTGGGCTTCAACCTG
GTGTGTACAGTGAGCCTGACCGAGTGTAGCGCCTTCCTGACCAGCATCAA
AGCCTGTGACGCCGCCATGTGTTACGGCAGCACCACCGCCAACCTGGTGA
GAGGCCAGAACACCATCCACATTGTGGGCAAAGGCGGCCACAGCGGCAGC
AAGTTTATGTGCTGCCACGACACCAAGTGTAGCAGCACCGGCCTGGTGGC
CGCTGCCCCCCACCTGGACAGAGTGACCGGCTACAACCAGGCCGACAGCG
ACAAGATTTTCGACGACGGAGCCCCTGAGTGTGGCATGAGTTGCTGGTTC
AAGAAGAGCGGCGAGTGGATTCTGGGCGTGCTGAACGGGAATTGGATGGT
GGTGGCCGTGCTGGTCGTGCTGCTGATCCTGAGCATCCTGCTGTTCACCC
TGTGCTGCCCTAGGAGACCCAGCTACCGGAAGGAGCACAAGCCCTGA
```

The peptide encoded by SEQ ID NO:1, the novel product having five amino acid alterations, is set forth here, and referred to hereafter as SEQ ID NO:2. Both the DNA and amino acids of this invention are unique. It is noted that a BLAST search reveals that a number of published amino acid sequences differ by only 1 or 2 different amino acids (i.e., PUUV strain K27, strain DTK/Ufa-97, strain P360)—this may be considered advantageous since the glycoprotein expressed by the subject DNA sequence is quite authentic with few cloning artifacts to interfere with its ability to elicit neutralizing antibodies.

SEQ ID NO:2
- synthetic M gene product of SEQ ID NO: 1, showing five amino acid alterations in boxes.
MGELSPVCLYLLLQGLLLCNTGAARNLNELKMECPHTIRLGQGLVVGS

VELPSLPIQQVETLKLESSCNFDLHTSTAGQQSFTKWTWEIKGDLAENT

QASSTSFQTKSSEVNLRGLCLIPTLVVETAARMRKTIACYDLSCNQTVC

QPTVYLMGPIQTCITTKSCLLSLGDQRIQVNYEKTYCVSGQLVEGICFN

PIHTMALSQPS[H]TYDIMTMMVRCFLVIKKVTSGDSMKIEKNFETLVQK

NGCTANNFQGYYICLIGSSSEPLYVPLADDYRSAEVLSRMAFAPHGED

-continued

HDIEKNAVSAMRIAGKVTGKAPSTESSDTVQGIAFSGSPLYTSTGVLTS

KDDPVYIWAPGIIMEGNHSICEKKTLPLTWTGFISLPGEIEKTTQCTVFC

TLAGPGADCEAYSETGIFNISSPTCLINRVQRFRGSEQQIKFVCQRVDM

DITVYCNGMKKVILTKTLVIGQCIYTFTSIFSLIPGVAHSLAVELCVPGL

HGWATMLLLLTFCFGWVLIPTITMILLKILIAFAYLCSKYNTDSKFRILIE

KVKREYQKTMGSMVCEVCQYECETAKELESHRKSCSIGSCPYCLNPSE

ATTSALQAHFKVCKLTSRFQENLRKSLTVYEPMQGCYRTLSLFRYRSR

FFVGLVWCVLLVLELIVWAASAETQNLNAGWTDTAHGSGIIPMKTDLE

LDFSLPSSASYTYRRQLQNPANEQEKIPFHLQLSKQVIHAEIQHLGHWM

DATFNLKTAFHCYGSCEKYAYPWQTAGCFIEDKYEYETGWGCNPPDC

PGVGTGCTACGVYLDKLKSVGKVFKIVSLRYTRKVCIQLGTEQTCKTV

DSNDCLITTSVKVCLIGTISKFQPSDTLLFLGPLQQGGLIFKQWCTTTCQ

FGDPGDIMSTPTGMKCPELNGSFRKKCAFATTPVCQFDGNTISGYKRM

IATKDSFQSFNVTEPHISTSALEWIDPDSSLRDHINVIVSRDLSFQDLSET

PCQIDLATASIDGAWGSGVGFNLVCTVSLTECSAFLTSIKACDAAMCY

GSTTANLVRGQNTIHIVGKGGHSGSKFMCCHDTKCSSTGLVAAAPHLD

RVTGYNQADSDKIFDDGAPECGMSCWFKKSGEWILGVLNGNWMVV

AVLVVLLILSILLFTLCCPRRPSYRKEHKP

In another embodiment, the invention entails a recombinant DNA construct comprising:
(i) a vector, and
(ii) the DNA fragment comprising the nucleic acid sequence set forth in SEQ ID NO:1, or a DNA fragment comprising a nucleic acid sequence that encodes the amino acid sequence set forth in SEQ ID NO:2.

As would be understood by someone having skill in this art, the DNA constructs of our invention will have all necessary structural components for expression of the DNA fragment of interest (e.g., promoters functional in mammals, and the like). The vector can take the form of a plasmid such as pCRII (Invitrogen) or pJW4303 (Konishi, E. et al., 1992, *Virology* 188:714), or any expression vector such as viral vectors e.g. adenovirus or Venezuelan equine encephalitis virus and others known in the art. Preferably, a promoter sequence operable in the target cell is operably linked to the DNA sequence. Several such promoters are known for mammalian systems which may be joined 5', or upstream, of the coding sequence for the encoded protein to be expressed. A suitable promoter is the human cytomegalovirus immediate early promoter. A downstream transcriptional terminator, or polyadenylation sequence, such as the polyA addition sequence of the bovine growth hormone gene, may also be added 3' to the protein coding sequence.

Preferably, the construct is the pWRG/PUU-M(s2) DNA vaccine plasmid, whose sequence is set forth below and referred to as SEQ ID NO:3. In SEQ ID NO:3, the underlined sequence is the codon-optimized open reading frame. The first bold sequence is the Not I cloning site and the second bold sequence is the Bam HI/Bgl II site. The synthetic open reading frame and flanking sequence was cloned into the Not I, Bgl II site of pWRG7077 (published). The flanking sequences include 5' and 3' non-translated sequence from the PUUV M genome segment, and a 24-base sequence between the Not I site and position +1 of the M gene. This sequence was found to be essential for expression of the Gn protein from the Hantaan virus and Seoul virus full-length M gene-based DNA vaccine plasmids, pWRG/HTN-M(x) and pWRG/SEQ-M, respectably. It is noted that experiments demonstrated that this 24-base sequence was not essential for expression of Gn from the PUUV M gene-based DNA vaccine plasmid, but was retained in this construct.

SEQ ID NO: 3
-- pWRG/PUU-M(s2) DNA vaccine plasm id
GGGGGGGGGGGGCGCTGAGGTCTGCCTCGTGAAGAAGGTGTTGCTGACTC

ATACCAGGCCTGAATCGCCCCATCATCCAGCCAGAAAGTGAGGGAGCCAC

GGTTGATGAGAGCTTTGTTGTAGGTGGACCAGTTGGTGATTTTGAACTTT

TGCTTTGCCACGGAACGGTCTGCGTTGTCGGGAAGATGCGTGATCTGATC

CTTCAACTCAGCAAAAGTTCGATTTATTCAACAAAGCCGCCGTCCCGTCA

AGTCAGCGTAATGCTCTGCCAGTGTTACAACCAATTAACCAATTCTGATT

AGAAAAACTCATCGAGCATCAAATGAAACTGCAATTTATTCATATCAGGA

TTATCAATACCATATTTTTGAAAAAGCCGTTTCTGTAATGAAGGAGAAAA

CTCACCGAGGCAGTTCCATAGGATGGCAAGATCCTGGTATCGGTCTGCGA

TTCCGACTCGTCCAACATCAATACAACCTATTAATTTCCCCTCGTCAAAA

ATAAGGTTATCAAGTGAGAAATCACCATGAGTGACGACTGAATCCGGTGA

GAATGGCAAAAGCTTATGCATTTCTTTCCAGACTTGTTCAACAGGCCAGC

CATTACGCTCGTCATCAAAATCACTCGCATCAACCAAACCGTTATTCATT

CGTGATTGCGCCTGAGCGAGACGAAATACGCGATCGCTGTTAAAAGGACA

ATTACAAACAGGAATCGAATGCAACCGGCGCAGGAACACTGCCAGCGCAT

CAACAATATTTTCACCTGAATCAGGATATTCTTCTAATACCTGGAATGCT

GTTTTCCCGGGGATCGCAGTGGTGAGTAACCATGCATCATCAGGAGTACG

GATAAAATGCTTGATGGTCGGAAGAGGCATAAATTCCGTCAGCCAGTTTA

GTCTGACCATCTCATCTGTAACATCATTGGCAACGCTACCTTTGCCATGT

TTCAGAAACAACTCTGGCGCATCGGGCTTCCCATACAATCGATAGATTGT

CGCACCTGATTGCCCGACATTATCGCGAGCCCATTTATACCCATATAAAT

CAGCATCCATGTTGGAATTTAATCGCGGCCTCGAGCAAGACGTTTCCCGT

TGAATATGGCTCATAACACCCCTTGTATTACTGTTTATGTAAGCAGACAG

TTTTATTGTTCATGATGATATATTTTTATCTTGTGCAATGTAACATCAGA

GATTTTGAGACACAACGTGGCTTTCCCCCCCCCCCGGCATGCCTGCAGG

TCGACAATATTGGCTATTGGCCATTGCATACGTTGTATCTATATCATAAT

ATGTACATTTATATTGGCTCATGTCCAATATGACCGCCATGTTGACATTG

ATTATTGACTAGTTATTAATAGTAATCAATTACGGGGTCATTAGTTCATA

GCCCATATATGGAGTTCCGCGTTACATAACTTACGGTAAATGGCCCGCCT

GGCTGACCGCCCAACGACCCCCGCCCATTGACGTCAATAATGACGTATGT

TCCCATAGTAACGCCAATAGGGACTTTCCATTGACGTCAATGGGTGGAGT

ATTTACGGTAAACTGCCCACTTGGCAGTACATCAAGTGTATCATATGCCA

AGTCCGCCCCCTATTGACGTCAATGACGGTAAATGGCCCGCCTGGCATTA

```
TGCCCAGTACATGACCTTACGGGACTTTCCTACTTGGCAGTACATCTACG
TATTAGTCATCGCTATTACCATGGTGATGCGGTTTTGGCAGTACACCAAT
GGGCGTGGATAGCGGTTTGACTCACGGGGATTTCCAAGTCTCCACCCCAT
TGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTT
GGCTCTTATGCATGCTATACTGTTTTTGGCTTGGGGCCTATACACCCCCG
CTTCCTTATGCTATAGGTGATGGTATAGCTTAGCCTATAGGTGTGGGTTA
TTGACCATTATTGACCACTCCCCTATTGGTGACGATACTTTCCATTACTA
ATCCATAACATGGCTCTTTGCCACAACTATCTCTATTGGCTATATGCCAA
TACTCTGTCCTTCAGAGACTGACACGGACTCTGTATTTTTACAGGATGGG
GTCCCATTTATTATTTACAAATTCACATATACAACAACGCCGTCCCCCGT
GCCCGCAGTTTTTATTAAACATAGCGTGGGATCTCCACGCGAATCTCGGG
TACGTGTTCCGGACATGGGCTCTTCTCCGGTAGCGGCGGAGCTTCCACAT
CCGAGCCCTGGTCCCATGCCTCCAGCGGCTCATGGTCGCTCGGCAGCTCC
TTGCTCCTAACAGTGGAGGCCAGACTTAGGCACAGCACAATGCCCACCAC
CACCAGTGTGCCGCACAAGGCCGTGGCGGTAGGGTATGTGTCTGAAAATG
AGCTCGGAGATTGGGCTCGCACCGCTGACGCAGATGGAAGACTTAAGGCA
GCGGCAGAAGAAGATGCAGGCAGCTGAGTTGTTGTATTCTGATAAGAGTC
AGAGGTAACTCCCGTTGCGGTGCTGTTAACGGTGGAGGGCAGTGTAGTCT
GAGCAGTACTCGTTGCTGCCGCGCGCCACCAGACATAATAGCTGACAG
ACTAACAGACTGTTCCTTTCCATGGGTCTTTTCTGCAGTCACCGTCCAAG
CTTGCGGCCGCGGATCTGCAGGAATTCGGCACGAGAGTAGTAGACTCCGC
AAGAAACAGCAAACACAGATAAATATGGGCGAGCTGTCCCTGTGTGCCT
GTACCTGCTGCTGCAGGGCCTGCTGCTGTGTAACACCGGAGCCGCCAGGA
ACCTGAACGAGCTGAAGATGGAGTGCCCCCACACCATCAGACTGGGCCAG
GGCCTGGTGGTGGGCAGCGTGGAGCTGCCCAGCCTGCCCATCCAGCAGGT
GGAGACCCTGAAGCTGGAGAGCAGCTGTAACTTCGACCTGCACACCAGCA
CAGCCGGCCAGCAGAGCTTCACCAAGTGGACCTGGGAGATCAAGGGCGAC
CTGGCCGAGAACACCCAGGCCAGCAGCACCAGCTTCCAGACCAAGAGCAG
CGAGGTGAACCTGAGAGGCCTGTGCCTGATCCCCACACTGGTGGTGGAGA
CCGCCGCCAGAATGAGAAAGACCATCGCCTGCTACGACCTGAGCTGTAAC
CAGACCGTGTGTCAGCCTACCGTGTACCTGATGGGCCCTATCCAGACCTG
TATCACCACCAAGAGCTGCCTGCTGTCCCTGGGCGATCAGAGAATCCAGG
TGAACTACGAGAAAACCTACTGTGTGAGCGGCCAGCTGGTGGAGGGCATC
TGCTTCAACCCCATCCACACCATGGCCCTGAGCCAGCCTAGCCACACCTA
CGACATCATGACCATGATGGTGAGATGCTTTCTGGTGATCAAGAAGGTGA
CCAGCGGCGACAGCATGAAGATCGAGAAGAACTTCGAGACCCTGGTGCAG
AAGAATGGCTGTACCGCCAACAACTTCCAGGGCTACTACATCTGCCTGAT
CGGCAGCAGCAGCGAGCCCCTGTACGTGCCCGCCCTGGACGACTACAGAA
GCGCCGAGGTGCTGTCCAGAATGGCCTTCGCCCCCACGGCGAGGACCAC
GACATCGAGAAAACGCCGTGTCCGCCATGAGAATCGCCGGCAAGGTGAC
CGGCAAGGCCCCCAGCACCGAGTCCAGCGACACCGTGCAGGGCATCGCCT
TCAGCGGCAGCCCCTGTACACCTCCACCGGCGTGCTGACCAGCAAGGAC
GACCCCGTGTACATCTGGGCCCCTGGCATCATCATGGAGGGCAACCACAG
CATCTGTGAGAAGAAACCCTGCCCCTGACCTGGACCGGCTTCATCAGCC
TGCCCGGCGAGATCGAGAAAACCACCCAGTGTACCGTGTTCTGTACCCTG
GCCGGACCTGGCGCCGACTGTGAGGCCTACAGCGAGACCGGCATCTTCAA
CATCAGCAGCCCCACCTGCCTGATCAACCGGGTGCAGAGGTTCAGAGGCA
GCGAGCAGCAGATCAAGTTTGTGTGCCAGCGGGTGGACATGGACATCACC
GTGTACTGTAACGGCATGAAGAAGGTGATCCTGACCAAGACACTGGTGAT
CGGCCAGTGTATCTACACCTTCACCAGCATCTTCTCCCTGATCCCCGGCG
TGGCCCACAGCCTGGCCGTGGAGCTGTGTGTGCCCGGCCTGCACGGCTGG
GCCACCATGCTGCTGCTGCTGACCTTCTGCTTCGGCTGGGTGCTGATCCC
TACCATCACCATGATCCTGCTGAAGATCCTGATCGCCTTCGCCTACCTGT
GCTCCAAGTACAACACCGACAGCAAGTTCAGAATCCTGATCGAGAAAGTG
AAGCGGGAGTACCAGAAAACCATGGGCAGCATGGTGTGTGAAGTGTGCCA
GTACGAGTGTGAGACCGCCAAGGAGCTGGAGTCCCACAGAAAGAGCTGCT
CCATCGGCAGCTGCCCCTACTGCCTGAACCCCAGCGAGGCCACCACCTCC
GCCCTGCAGGCCCACTTCAAAGTGTGTAAGCTGACCAGCCGGTTCCAGGA
GAACCTGAGGAAGTCCCTGACCGTGTACGAGCCCATGCAGGGCTGCTACA
GAACCCTGAGCCTGTTCCGGTACAGGAGCCGGTTCTTTGTGGGCCTGGTG
TGGTGTGTGCTGCTGGTGCTGGAGCTGATTGTGTGGGCCGCCAGCGCCGA
GACCCAGAACCTGAATGCCGGCTGGACCGACACCGCCCACGGCAGCGGCA
TCATCCCCATGAAAACCGACCTGGAGCTGGACTTCAGCCTGCCTAGCAGC
GCCTCCTACACCTACAGGCGGCAGCTGCAGAATCCTGCCAACGAGCAGGA
GAAGATCCCCTTCCACCTGCAGCTGTCCAAGCAGGTGATCCACGCCGAGA
TTCAGCACCTGGGCCACTGGATGGACGCCACCTTCAACCTGAAAACCGCC
TTCCACTGCTACGGCAGCTGTGAAGTACGCCTACCCTTGGCAGACCGC
CGGCTGCTTCATCGAGAAGGACTACGAGTACGAGACCGGCTGGGGCTGTA
ATCCTCCTGATTGCCCCGGAGTGGGCACCGGCTGTACTGCATGTGGCGTG
TACCTGGACAAGCTGAAGTCTGTGGGCAAGGTGTTCAAGATCGTGTCCCT
GAGGTACACCCGGAAAGTGTGTATCCAGCTGGGCACCGAGCAGACCGTA
AGACCGTGGACAGCAACGATTGCCTGATCACAACCAGCGTGAAAGTGTGT
CTGATCGGCACCATCAGCAAGTTCCAGCCCAGCGATACCCTGCTGTTTCT
GGGCCCCCTGCAGCAGGGCGGCCTGATCTTCAAGCAGTGGTGTACCACCA
CCTGCCAGTTCGGCGATCCCGGCGATATCATGAGCACCCCCACCGGCATG
AAGTGCCCTGAGCTGAACGGCAGCTTCCGGAAGAAGTGTGCCTTCGCCAC
CACCCCTGTGTGTCAGTTCGACGGCAACACCATCAGCGGCTACAAGCGGA
```

```
-continued
TGATCGCCACCAAGGACAGCTTCCAGTCCTTCAACGTGACCGAGCCCCAC

ATCAGCACCAGCGCCCTGGAGTGGATCGATCCCGACAGCAGCCTGAGGGA

CCACATCAACGTGATCGTGTCCAGGGACCTGAGCTTCCAGGACCTGAGCG

AGACCCCCTGCCAGATCGACCTGGCCACCGCCAGCATCGATGGCGCCTGG

GGCAGCGGAGTGGGCTTCAACCTGGTGTGTACAGTGAGCCTGACCGAGTG

TAGCGCCTTCCTGACCAGCATCAAAGCCTGTGACGCCGCCATGTGTTACG

GCAGCACCACCGCCAACCTGGTGAGAGGCCAGAACACCATCCACATTGTG

GGCAAAGGCGGCCACAGCGGCAGCAAGTTTATGTGCTGCCACGACACCAA

GTGTAGCAGCACCGGCCTGGTGGCCGCTGCCCCCCACCTGGACAGAGTGA

CCGGCTACAACCAGGCCGACAGCGACAAGATTTTCGACGACGGAGCCCCT

GAGTGTGGCATGAGTTGCTGGTTCAAGAAGAGCGGCGAGTGGATTCTGGG

CGTGCTGAACGGGAATTGGATGGTGGTGGCCGTGCTGGTCGTGCTGCTGA

TCCTGAGCATCCTGCTGTTCACCCTGTGCTGCCCTAGGAGACCCAGCTAC

CGGAAGGAGCACAAGCCCTGAGTTTTGCTTACTAACATAATTATTGTATT

CTGTTTATTGACACAATTACCATATGATTAACTGTATTCCCCCATCTTAT

ATCTTATATAATATTCTTTATTTAATCACTATATAGAAAAAAAACTAGCA

CTTTACTAATTAAATTACCCCATACCGATTATGCCTGGACTTTTGTTCCT

GCGGAGCATACTACTAGGATCTACGTATGATCAGCCTCGACTGTGCCTTC

TAGTTGCCAGCCATCTGTTGTTTGCCCCTCCCCCGTGCCTTCCTTGACCC

TGGAAGGTGCCACTCCCACTGTCCTTTCCTAATAAAATGAGGAAATTGCA

TCGCATTGTCTGAGTAGGTGTCATTCTATTCTGGGGGGTGGGGTGGGGCA

GGACAGCAAGGGGAGGATTGGGAAGACAATAGCAGGCATGCTGGGGATG

CGGTGGGCTCTATGGCTTCTGAGGCGGAAAGAACCAGCTGGGGCTCGACA

GCTCGACTCTAGAATTGCTTCCTCGCTCACTGACTCGCTGCGCTCGGTCG

TTCGGCTGCGGCGAGCGGTATCAGCTCACTCAAAGGCGGTAATACGGTTA

TCCACAGAATCAGGGGATAACGCAGGAAAGAACATGTGAGCAAAAGGCCA

GCAAAAGGCCAGGAACCGTAAAAAGGCCGCGTTGCTGGCGTTTTTCCATA

GGCTCCGCCCCCTGACGAGCATCACAAAAATCGACGCTCAAGTCAGAGG

TGGCGAAACCCGACAGGACTATAAAGATACCAGGCGTTTCCCCCTGGAAG

CTCCCTCGTGCGCTCTCCTGTTCCGACCCTGCCGCTTACCGGATACCTGT

CCGCCTTTCTCCCTTCGGGAAGCGTGGCGCTTTCTCATAGCTCACGCTGT

AGGTATCTCAGTTCGGTGTAGGTCGTTCGCTCCAAGCTGGGCTGTGTGCA

CGAACCCCCGTTCAGCCCGACCGCTGCGCCTTATCCGGTAACTATCGTC

TTGAGTCCAACCCGGTAAGACACGACTTATCGCCACTGGCAGCAGCCACT

GGTAACAGGATTAGCAGAGCGAGGTATGTAGGCGGTGCTACAGAGTTCTT

GAAGTGGTGGCCTAACTACGGCTACACTAGAAGAACAGTATTTGGTATCT

GCGCTCTGCTGAAGCCAGTTACCTTCGGAAAAAGAGTTGGTAGCTCTTGA

TCCGGCAAACAAACCACCGCTGGTAGCGGTGGTTTTTTTGTTTGCAAGCA

GCAGATTACGCGCAGAAAAAAAGGATCTCAAGAAGATCCTTTGATCTTTT

CTACGGGGTCTGACGCTCAGTGGAACGAAAACTCACGTTAAGGGATTTTG

GTCATGAGATTATCAAAAAGGATCTTCACCTAGATCCTTTTAAATTAAAA
```

```
-continued
ATGAAGTTTTAAATCAATCTAAAGTATATATGAGTAAACTTGGTCTGACA

GTTACCAATGCTTAATCAGTGAGGCACCTATCTCAGCGATCTGTCTATTT

CGTTCATCCATAGTTGCCTGACTC
```

In a further embodiment, the present invention relates to host cells stably transformed or transfected with the above-described recombinant DNA constructs. The host cell can be prokaryotic such as *Bacillus* or *E. coli*, or eukaryotic such a *Saccharomyces* or *Pichia*, or mammalian cells or insect cells. The vector containing the Puumala virus M gene sequence is expressed in the bacteria and the expressed product used for diagnostic procedures or as a vaccine. Please see e.g., Maniatis et al., 1985 *Molecular Cloning: A Laboratory Manual* or *DNA Cloning*, Vol. I and II (D. N. Glover, ed., 1985) for general cloning methods. The DNA sequence can be present in the vector operably linked to a highly purified IgG molecule, an adjuvant, a carrier, or an agent for aid in purification of Puumala virus proteins or peptides. The transformed or transfected host cells can be used as a source of DNA sequences described above. When the recombinant molecule takes the form of an expression system, the transformed or transfected cells can be used as a source of the protein or peptide encoded by the DNA. The DNA can be used as circular or linear, or linearized plasmid as long as the Puumala virus sequences are operably linked to a promoter which can be expressed in the transfected cell.

In another embodiment, the invention entails vaccines against infection with Puumala virus. As shown below, the DNA vaccine is able to cross-neutralize against PUUV strains from different geographic regions. Thus, it would be effective to protect against strains such as Sotkamo, and Russian strains including K27 and P360. The vaccine may involve the delivery of pWRG/PUU-M(s2) DNA by any of several platforms used to deliver gene-based molecular vaccines. For example, the vaccine could comprise a composition comprising inert particles and a nucleic acid coated onto the inert particles producing nucleic acid coated particles. The nucleic acid will comprise a promoter operative in the cells of a mammal and further comprise (or even consist essentially of or consist of) SEQ ID NO:1. As would be understood by someone having skill in this art, the ORF sequence (SEQ ID NO:1) is essential. The flanking region between the cloning sites and the ORF are preferably includes, as they may be helpful for efficient expression. Also, 5' and/or 3' noncoding PUU-M sequence may be includes, since it may also be helpful and experiments excluding them have not been performed. The inert particle may be gold particles, silver particles, platinum particles, tungsten particles, polystyrene particles, polypropylene particles, polycarbonate particles, and the like, as would be understood by someone having ordinary skill in this art. In particular, it is preferred that the inert particle is suitable for use in a gene gun.

To that end, the invention further encompasses a method for inducing a protective immune response against Puumala virus infection in a mammal, comprising the step of accelerating into epidermal cells of the mammal in vivo a composition comprising inert particles and a nucleic acid coated onto the inert particles producing nucleic acid coated particles, such that said nucleic acid is expressed. The nucleic acid will comprise a promoter operative in the cells of a mammal and SEQ ID NO:1. The nucleic acid may further include the flanking sequence of SEQ ID NO:1 as designated in SEQ ID NO:3, from the Not1 site to the BamH1/BglII site—this has been shown to be effective in a vaccine.

The Puumala M gene cassette in the pWRG/PUU-M (s2) plasmid (preferably taken from the Not 1 site to the BamH1/BglII site, or minimally the ORF operably linked to a promoter) can be subcloned into any other vaccine/expression system available, and used to generate active or passive immunity against Puumala virus. The DNA cassette specifically includes at least SEQ ID NO:1 linked to a promoter operable in a eukaryotic expression system. Preferably, the DNA cassette includes the sequence in SEQ ID NO:3 (within pWRG/PUU-M(s2)) from the Not I cloning site to the Bam HI/Bgl II site of pWRG7077. Thus, in another embodiment, the invention encompasses a DNA cassette comprising only the PUUV M gene ORF within pWRG/PUU-M(s2).

In a more general method for inducing a protective immune response against Puumala virus infection in a mammal, a composition is administered to a mammal comprising a nucleic acid comprising a promoter operative in the cells of a mammal and SEQ ID NO: 1.

The invention also encompasses passive vaccines for treating or preventing Puumala virus infections. Polyclonal antibodies may be obtained using methods known in the art, from a population of vaccinees vaccinated with a Puumala virus DNA vaccine comprised of a plasmid expressing SEQ ID NO:1, such as pWRG/PUU-M(s2). Alternatively, polyclonal or monoclonal antibodies could be produced in animals using the pWRG/PUU-M(s2) plasmid. The methods entail administration of a therapeutically or prophylactically effective amount of the antibodies which protect against Puumala virus disease in combination with a pharmaceutically acceptable carrier or excipient. For instance, a therapeutic composition for ameliorating symptoms of Puumala virus infection may comprise a composition comprising these polyclonal antibodies, and a pharmaceutically acceptable excipient. For instance, pWRG/PUU-M(s2) may be used to vaccinate ducks or transgenic cows to produce polyclonal neutralizing antibodies for use in humans.

The invention also entails a method for diagnosis of Puumala virus infection by assaying for the presence of Puumala virus in a sample using the above-described antibodies. For instance, a method for the diagnosis of Puumala virus infection may comprise the steps of:

(i) contacting a sample from an individual suspected of having Puumala virus infection with a composition comprising the polyclonal antibodies (e.g., the pWRG/PUU-M(s2) plasmid could be used to produce diagnostic antibodies in any of several species of animals-goats, rabbits, etc.); and (ii) detecting the presence or absence of Puumala virus infection by detecting the presence or absence of a complex formed between Puumala virus antigens and antibodies specific therefor.

In addition, the invention encompasses novel immunoprobes and test kits for detection of Puumula virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to Puumula virus to form an immunological complex and detecting the formation of the immunological complex such that presence or absence of the immunological complex correlates with presence or absence of Puumula virus. For instance, the kit may include the above-described polyclonal antibodies, and ancillary reagents suitable for use in detecting the presence or absence of Puumala virus antigens in a sample.

Further, the invention contemplates a method for producing pseudotyped viruses for use in serologic assays or delivery of gene therapies to endothelial cells targeted by hantavirus glycoproteins. The invention as used for this purpose would comprise the following steps. The plasmid pWRG/PUU-M(s2) or derivative thereof would be used to transfect cells or stably transform cells. Cells expressing the PUUV glycoproteins could then be infected with viruses engineered to produce progeny that incorporate the PUUV glycoproteins into progeny virus surface envelopes. Pseudotype virus systems include retrovirus systems and vesicular stomatitis virus systems. Pseudotypes have been produced using the hantavirus full-length M gene plasmids, including pWRG/PUU-M (s2). The pseudotypes can be used for testing for neutralizing antibodies. They also may be used to deliver genes to endothelial cells in a clinical setting. For example, gene therapy viruses containing the PUUV glycoproteins on their surface will target to certain endothelial cells.

The invention is described in further detail by the non-limiting examples and text below.

BRIEF DESCRIPTION OF THE FIGURES

FIG. 1 shows how PUUV DNA vaccine elicits neutralizing antibodies in hamsters. Hamsters #326 thru #333 were vaccinated with the Hantaan virus DNA vaccine, pWRG/HTN-M(x) and hamsters #334 thru #342 were vaccinated with the Puumala virus DNA vaccine, pWRG/PUU-M(s2). HTNV and PUUV PRNT were performed on all serum samples collected 3 weeks after the last vaccination. Note lack of cross neutralizing activity. Dashed line indicates lowest dilution tested, 1:20.>indicates endpoint titer not determined.

FIG. 2. Hamsters were vaccinated with PUUV DNA vaccine, pWRG/PUU-M(s2) in ND10 devices (PUU ND10), HTNV DNA vaccine, pWRG/HTN-M(x) in ND10 devices (HTN ND10), or were not vaccinated (None). At 1 or 4 months after the last vaccination the hamsters were challenged. Five weeks later sera were collected and evaluated for anti-N antibody. The presence of anti-N antibody indicates that the animal was infected with PUUV, i.e., the animal was not protected. Each symbol represents the average anti-N ELISA titer for a single hamster. The GMT+/−95% confidence interval for each group is shown.

FIG. 4. This shows the neutralization of PUUV strain Sotkamo, and specifically pWRG/PUU-M(s2) DNA vaccine elicits neutralizing antibodies that cross-neutralize a divergent strain of PUUV (Sotkamo) from a geographically distinct region. Three cynomolgus macaques were vaccinated with the candidate PUUV DNA vaccine, pWRG/PUU-M(s2), or with earlier candidate plasmids, pWRG/PUU-M(s1) and pWRG/PUU-M-(x22). Sera collect after 3 or 4 vaccinations was tested for a capacity to neutralize PUUV, strain Sotkamo. The PRNT50 titer is proved. The limit of detection was a titer of 20 (dashed line).

DETAILED DESCRIPTION OF THE INVENTION

Figure 3:
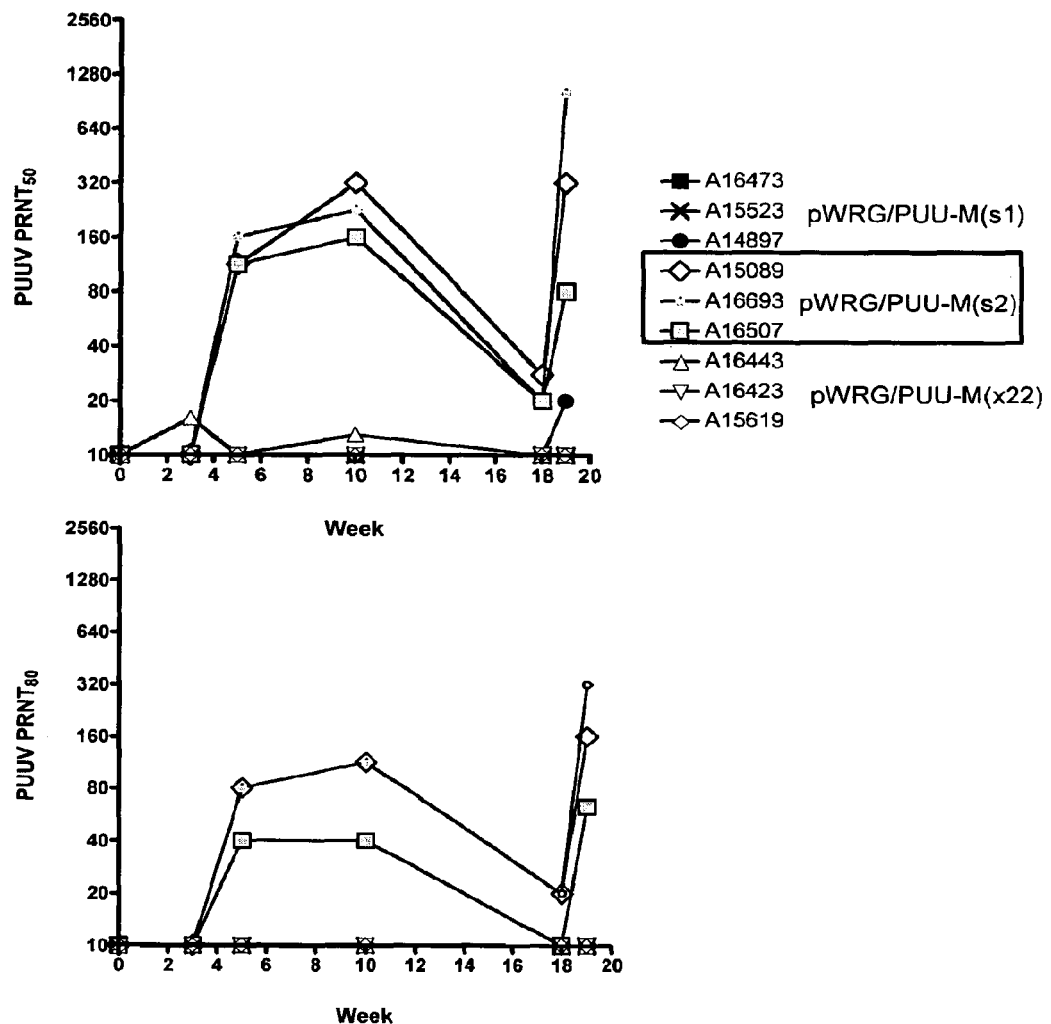
FIG. 3A (top) and 3B (bottom). This shows how pWRG/PUU-M(s2) DNA vaccine elicits neutralizing antibodies in nonhuman primates. Three cynomolgus macaques were vaccinated with the candidate PUUV DNA vaccine, pWRG/PUU-M(s2), or with earlier candidate plasmids, pWRG/PUU-M(s1) and pWRG/PUU-M-(x22). Arrows indicate the week when PMED vaccination was administered. The pWRG/PUU-M(s2) vaccine elicited neutralizing antibodies; whereas, the other two plasmids produced low or undetected levels of neutralizing antibodies. $PRNT_{50}$ titers are shown in the top panel, and $PRNT_{80}$ are shown in the bottom panel. $PRNT_{50}$ titer and $PRNT_{80}$ titers=the reciprocal of the highest serum dilution that reduced plaque number by 50% or 80% relative to the number of plaques in no serum control wells.

Supplemental to the previous description of the invention, the following further details are provided. As noted above, attempts to produce molecular vaccines that produce neutralizing antibodies against PUUV have been unsuccessful. Here, for the first time, the inventor have synthesized a codon-optimized full-length M gene open reading frame and cloned it into a DNA vaccine expression vector (e.g., pWRG/PUU-M(s2)). The amino acid sequence was similar but not identical to published strains of PUUV isolated in Russia (e.g. K27, P360, Bashkortustan). The nucleotide sequences is completely unique because the ORF has been optimized. Hamsters vaccinated with pWRG/PUU-M(s2) using a gene gun developed neutralizing antibodies as measured by plaque reduction neutralization test (PRNT) with $PRNT_{50}$ titers ranging from 320 to 10,240. Similarly, nonhuman primates vaccinated with pWRG/PUU-M(s2), but not a plasmid with 5 amino acid substitutions, produced neutralizing antibodies with $PRNT_{50}$ ranging from 320 to 640 after a single booster vaccination. This is believed to be the first candidate molecular vaccine that successfully elicits neutralizing antibodies against PUUV.

In its preferred vaccine embodiment, the Puumala virus M gene-based DNA vaccine is a plasmid that consists of a well-characterized backbone that enables expression of the above-described synthentic, codon-optimized, Puumala virus full-length M gene. It can be used in other molecular vaccine systems and systems for generating Puumala virus neutralizing antibodies.

Construction of pWRG/PUU-M(s2) was performed as follows: A consensus sequence of the M genome segment of Puumala virus strain K27 was determined by sequencing partial and full clones of the gene obtained in the inventor's laboratory (e.g., pWRG/PUU-M-(x22)), and the published sequence (GeneBank accession number L08754). The inventor prepared an in slico consensus amino acid sequence with 5' and 3' flanking nucleic acid sequence that included sequences identical to those used in pWRG/HTN-M(x). These flanking sequences included the polylinker remnants (2903-3028 of pWRG/HTN-M(x)) and the Seoul M gene fragment (3029-3709 of pWRG/HTN-M(x)). Using this gene and flanking sequences the gene was synthesized and the ORF was codon optimized. The resulting synthetic gene, 051399, was assembled from synthetic oligonucleotides. The fragment was cloned into the Not I and BglII site of plasmid pWRG7077. The resulting plasmid was designated pWRG/PUU-M(s2). The plasmid DNA was purified and sequenced. The sequence of pWRG/PUU-M(s2) is provided in SEQ ID NO:3.

Initially the inventor cloned the Gn, Gc, and full-length M gene of the K27 strain of PUUV into the mammalian DNA vaccine expression vector pWRG7077. These plasmids designated pWRG/PUU-G1, pWRG/PUU-G2, and pWRG/PUU-M-(x22) expressed the Gn, Gc and Gn and Gc glycoproteins, respectably, when transfected into cell culture (data not shown). Hamsters vaccinated with these plasmids did not develop detectable antibody responses and were not protected from infection when challenged with PUUV (data not shown). pWRG/PUU-M-(x22) was immunogenic in nonhuman primates as measured by the production of anti-Gn and anti-Gc antibodies; however, the neutralizing antibody response was low or undetectable (data not shown). The aforementioned data was reported at the XIII International Congress of Virology Meeting, July 2005.

In an attempt to improve the immunogenicity of the PUUV full-length M gene-based DNA vaccine, the amino acid sequence of our pWRG/PUU-M-(x22) clone was compared with published sequences and sequences we obtained from partial clones produced during early attempts to clone the full-length M gene. The inventor concluded that there were 5 amino acids that were probably incorrect substitutions produced during the cloning process. It was hypothesized that if these amino acid substitutions were replaced with consensus amino acids, then the conformation of the Gn-Gc oligomers might more accurately mimic authentic PUUV surface glycoproteins, and consequently might produce a more potent neutralizing antibody response. To test this, a PUUV M gene open reading frame was synthesized with the 5 amino acids changed to consensus amino acids. In addition, the open reading frame was codon-optimized. Codon optimization was performed to 1.) change the molecule sequence in an attempt to stabilize the plasmid (pWRG/PUU-M[x22] was toxic in *E. coli* and there was selective pressure that resulted in the production of mutated plasmid DNA during the production of maxiprep DNA), 2.) possibly increase the amount of Gn-Gc produced in transfected cells. A codon-optimized version of original plasmid, pWRG/PUU-M-(x22), was also synthesized and designated pWRG/PUU-M(s1).

In addition, the inventor had discovered that there were several nucleotide differences between the ORF in pWRG/PUU-M-(x22) and several of the partial clones they had obtained during earlier attempts to clone the intact full-length M gene ORF, as well as differences in their cloned sequence and the published Puumala virus strain K27 and other Russian strains. Five of these nucleotide changes resulted in amino acid substitutions that were unique to the M gene in pWRG/PUU-M-(x22), and a new clone was synthesized to test if these five amino acid changes altered the immunogenicity of the glycoproteins. A consensus amino acid, codon-optimized version of pWRG/PUU-M-(x22) was synthesized, designated pWRG/PUU-M(s2). The only difference between pWRG/PUU-M(s1) and pWRG/PUU-M(s2) were the nucleotide positions resulting in the 5 amino acid changes (relative to the amino acid sequence of the M gene in pWRG/PUU-M-(x22). Both clones were codon optimized. It was discovered that pWRG/PUU-M(s2), and not pWRG/PUU-M(s1), was effective in eliciting neutralizing antibodies to PUUV. Thus, while it is quite useful that the pWRG/PUU-M(s1) was codon optimized and therefore stable within the plasmid, it was necessary to have both codon optimization and the five amino acid alterations in order to stably express a synthetic protein product that would effectively elicit neutralizing antibodies to PUUV.

It was possible to scale up expression of pWRG/PUU-M (s2) pWRG/PUU-M (s2) expresses in cell culture and mobility of G2 glycoprotein is slightly different from the G2 expressed from pWRG/PUU-M (s1) or pWRG/PUU-M (s2). Immunofluorescence pattern is also different in transfected cells. Together these data indicates that the five amino acid differences have a dramatic effect on the biochemical and biological properties of the expression products p WRG/PUU-M (s2) elicits neutralizing antibodies in nonhuman primates. After two vaccinations using a gene gun, three out of three rhesus macaques seroconverted and the neutralizing antibody titers were relatively high (plaque reduction neutralization 80% titers [PRNT80] were 80-160. In contrast, 0 of 3 monkeys vaccinated with pWRG/PUU-M (s 1) and 0 out of 3 monkeys vaccinated 4 times with pWRG/PUU-M-(x22) exhibited PRNT80 titers 20. Monkeys primed with pWRG/

PUUM(x22) and then boosted one time with pWRG/PUU-M (s2) exhibited an increase in antibodies against G1 and G2 as measured by radioimmunoprecipitation and PRNT80 from 20-80.

As shown below, pWRG/PUU-M (s2) elicits neutralizing antibodies in small animal models. Eight out of eight hamsters developed neutralizing antibody titers after three vaccinations using a gene gun pWRG/PUU-M-(x22) did not elicit neutralizing antibodies in hamsters. In addition, pWRG/PUU-M (s2) elicits neutralizing antibodies when delivered by means other than gene gun. Rabbits vaccinated by muscle electroporation delivered high-titer neutralizing antibodies.

In Vitro Data Generated with pWRG/PUU-M(s2)

Empirical data indicate the pWRG/PUU-M(s2) is a more stable plasmid when replicating in *E. coli*. For example, large preparations of DNA, including GMP manufactured DNA have been manufactured without evidence of plasmid instability. It was concluded that the changes in the M gene open reading frame nucleic acid sequence that were made during the codon-optimization effectively removed the *E. coli*.-toxic sequences in pWRG/PUU-M-(x22).

The inventor tested pWRG/PUU-M(s2) for a capacity to express PUUV Gn and Gc after transfection into COS cells. Expression of the PUUV glycoproteins was detected by radio-immunoprecipitation (RIPA) or immunofluorescent antibody test (IFAT). RIPA indicated that both Gn and Gc were expressed. Interestingly, the Gn protein ran with a slightly faster mobility than the Gn from pWRG/PUU-M-(x22) or pWRG/PUU-M(s1). The small differences in the molecular weights of the substituted amino acids relative to the entire mass of the Gn protein does not account for this change in mobility.

Thus, one or more of the amino acid changes in Gn (4 of the 5 amino acid substitutions are in Gn) effectively changed the processing and/or conformation of the Gn protein. Similarly, the IFAT data indicate that the glycoproteins expressed from pWRG/PUU-M(s2) are different from those expressed from pWRG/PUU-M-(x22) or pWRG/PUU-M(s1). Whereas the expression pattern in pWRG/PUU-M(s2) transfected cells is punctate (i.e., what appears to be short aggregates of protein), the expression pattern in pWRG/PUU-M-(x22) and pWRG/PUU-M(s2) is diffuse (i.e., no short aggregates). Together these in vitro data indicated that the glycoproteins expressed from pWRG/PUU-M(s2) were biophysically different from pWRG/PUU-M-(x22) and might possibly elicit a different immune response in vaccinated animals (as originally hypothesized).

Immunogenicity of pWRG/PUU-M(S2) in Animals

The PUUV DNA vaccine, pWRG/PUU-M(s2) was tested in hamsters and nonhuman primates. In both species the vaccine elicited neutralizing antibodies.

Figure 1:
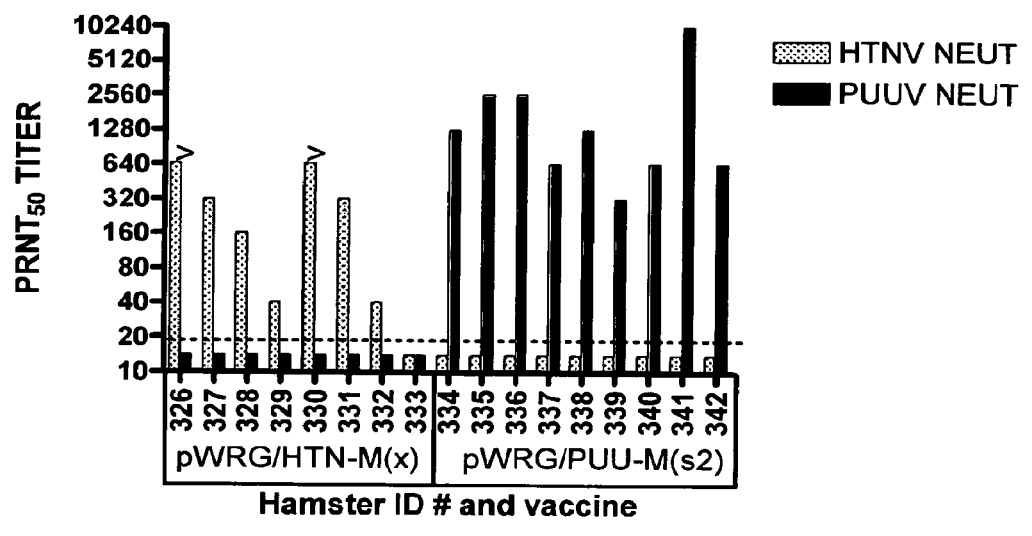

(1) Hamster experiments. Puumala virus (PUUV) M gene-based DNA vaccine has been shown to be immunogenic in hamsters. One group of 8 hamsters was vaccinated with pWRG/PUU-M(s2) three times at 2- to 3-week intervals using particle mediated epidermal delivery (PMED) with the XR-1 experimental device. A second group was vaccinated by the same schedule with the Hantaan DNA vaccine, pWRG/HTN-M(x). Each vaccination consisted of four ~1 µg DNA PMED administrations (~4 µg total DNA, 400 psi, per hamster per vaccination). Three weeks after the last vaccination, serum was collected and PUUV and HTNV PRNTs were performed. One hundred percent of the hamsters vaccinated with pWRG/PUU-M(s2) 3 times at 3-week intervals produced neutralizing antibodies. The PRNT$_{50}$ Geometric Mean Titer (GMT) was 1280. The range of titers was between 320 and 10,240. Seven of 8 hamsters vaccinated with pWRG/HTN-M(x) developed neutralizing antibodies with PRNT$_{50}$ titers ranging from 40 to >640. There was no cross-neutralizing activity in any of the serum samples. (FIG. 1).

During nonclinical studies an in vivo immunogenicity test was developed to assess the potency of the HTNV and PUUV DNA vaccines. The test involves vaccinating hamsters using a compressed schedule (i.e., vaccination on week 0, 2, and 3 and sera collection on week 4). Serum is tested for neutralizing antibodies by PRNT and the PRNT$_{50}$ titers for each animal are determined. The seroconversion rate (ratio of animals with titers ≥1:20 PRNT$_{50}$ to the total number of vaccinated animals), geometric mean titer, and median titer are also recorded. The ≥1:20 PRNT$_{50}$ endpoint was selected for two main reasons: (1) it is the lowest dilution that can be used to measure specific neutralizing antibody, and (2) animal studies show that a titer of 1:20 results in sterile immunity in nearly every case.

The combined results of seven in vivo immunogenicity tests of pWRG/HTN-M(x) in XR-1 devices manufactured at Powderject indicated that there was an 82% seroconversion rate (55 of 67 hamsters). Titers ranged from 20 to 2560. Recently both the HTNV and PUUV DNA vaccines in ND10 devices were shown to be immunogenic in hamsters. An in vivo immunogenicity test on GMP lots indicated that 100% and 80% of the hamsters vaccinated with HTNV and PUUV, respectively, seroconverted as measured by the production of neutralizing antibodies (USAMRIID unpublished data).

Protection in hamsters was also found using the DNA vaccines. For the hemorrhagic fever with renal syndrome (HFRS)-associated hantaviruses, protection was evaluated using infection models. Hamsters vaccinated with Seoul virus (SEOV) or HTNV M gene-based DNA vaccines protected hamsters against infection with three of the four HFRS-associated hantaviruses: HTNV, SEOV, and Dobrava virus (DOBV), but not PUUV [1]. In the aforementioned infection models, hamsters were vaccinated and then ~4 weeks after the last vaccination, the hamsters were challenged with 2,000 median infectious dose (ID$_{50}$) of the hantavirus of interest. Serum samples were collected just prior to challenge and then again 4-5 weeks later. Challenged hamsters that developed antibodies to *hantavirus* N protein (not a component of the vaccine) 4 weeks after challenge were considered to be infected. Conversely, hamsters that failed to develop an N-specific antibody response were considered not to be infected (i.e., protected from infection). A >4-fold increase in neutralizing antibody titer after challenge also served as a marker for evidence of infection.

Figure 2:
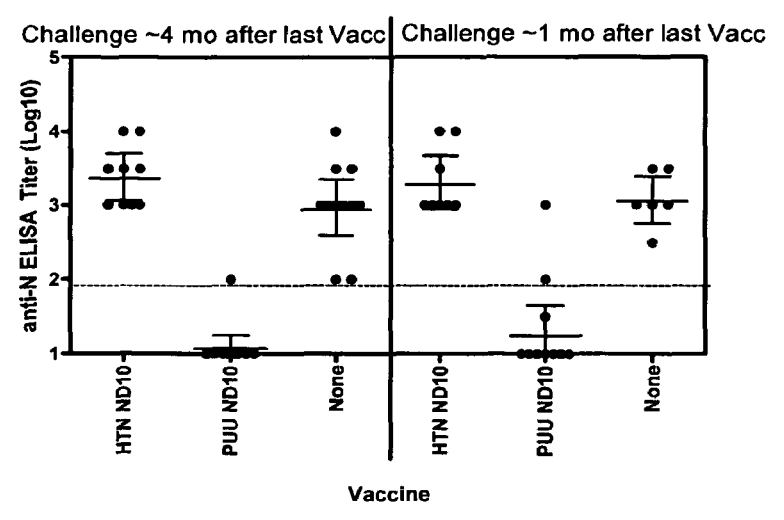

An experiment was performed evaluating the protective efficacy of the PUUV DNA vaccine, pWRG/PUU-M(s2). Hamsters were vaccinated with either the PUUV DNA vaccine (in ND10 devices, which are PowderMed's hand-held, disposable gene gun) or HTNV DNA vaccine (in ND10 devices) using the compressed schedule (week 0, 2, and 3). Vaccinated hamsters were then challenged intramuscularly with PUUV at either 1 or 4 months after the last vaccination. Groups of age-matched hamsters that were not vaccinated were included as negative controls. Five weeks after challenge, sera were collected and evaluated for evidence of infection by N protein ELISA (see FIG. 2). Hamsters (17 of 20) vaccinated with the PUUV DNA vaccine were protected (no anti-N antibody). In contrast, all hamsters that were not vaccinated (None) and hamsters vaccinated with the HTNV DNA vaccine were infected by PUUV (anti-N ELISA titers were >2). The latter finding confirmed that vaccination with the HTNV DNA vaccine does not cross-protect against PUUV. These data were the first demonstration that an M gene-based PUUV DNA vaccine could confer protective immunity in any model.

(2) Non-human primate (NHP) experiments. The PUUV M gene-based DNA vaccine was tested for immunogenicity in nonhuman primates. Three cynomolgus macaques were vaccinated with pWRG/PUU-M(s2) at Weeks 0, 3, and 8. Serum was collected on Weeks 0, 3, 5, and 10 and tested for neutralizing antibodies. In the same experiments, 3 monkeys per group were vaccinated with earlier versions of the PUUV M gene-based DNA vaccine (i.e., pWRG/PUU-M-(x22) and pWRG/PUU-M(s1)). pWRG/PUU-M-(x22) differs from pWRG/PUU-M(s2) at 5 amino acid positions. pWRG/PUU-M(s1) is identical to pWRG/PUU-M(s2) at the amino acid level, but the ORF (open reading frame) is codon optimized. All three nonhuman primates vaccinated with pWRG/PUU-M(s2) had detectable neutralizing antibody levels after the second vaccination (week 5 serum). The $PRNT_{50}$ titers ranged from 160 to 320. The titers remained essentially the same after the third vaccination ($PRNT_{50}$ ranged from 320 to 640). In contrast, none of the nonhuman primates vaccinated with pWRG/PUU-M-(x22) or pWRG/PUU-M(s1) produced neutralizing antibody titers >40 (FIG. 3).

To further evaluate the immunogenicity of the PUUV DNA vaccine candidates, the nonhuman primates were boosted again at Week 18. PRNT assays were performed on Week 18 and 19 sera. The levels of neutralizing antibodies in the nonhuman primates vaccinated with pWRG/PUU-M(s2) were still detectable, albeit low, 10 weeks after the last vaccination. After Week 18 booster vaccination, the titers rose to between 80 and 1280. Titers in the nonhuman primates vaccinated with pWRG/PUU-M-(x22) or pWRG/PUU-M(s1) remained low or below detection. In FIG. 3, $PRNT_{50}$ titers are shown in the top panel, and $PRNT_{80}$ titers are shown in the bottom panel.

Cross Neutralization of PUUV Strains from Different Geographic Regions

The inventor sought to determine if the sera from macaques vaccinated with the PUUV DNA vaccine constructs could neutralize the Sotkamo strain of PUUV. PUUV strain Sotkamo is a prototype Scandinavian *hantavirus* isolated in Finland. This was important because pWRG/PUU-M(s2) is based on the M gene of a Russian strain of PUUV, strain K27. There are several amino acid differences between the M gene in pWRG/PUU-M(s2) and strain Sotkamo and therefore it was possible that the antibodies elicited by the subject vaccine might not neutralize the Scandinavian strains of PUUV.

To test this the inventor performed plaque reduction neutralization tests using serum collected from nonhuman primates vaccinated with three different plasmids. Serum collected after the $3^{rd}$ of $4^{th}$ vaccination were tested using an assay were the plaques were visualized after immunostaining with a monoclonal antibody (MAb-3d7) that binds PUUV antigen. This immunostaining was used because PUUV strain Sotkamo produced poorly discernable plaques when neutral red was used. This assay is also called a foci reduction assay.

Figure 4:
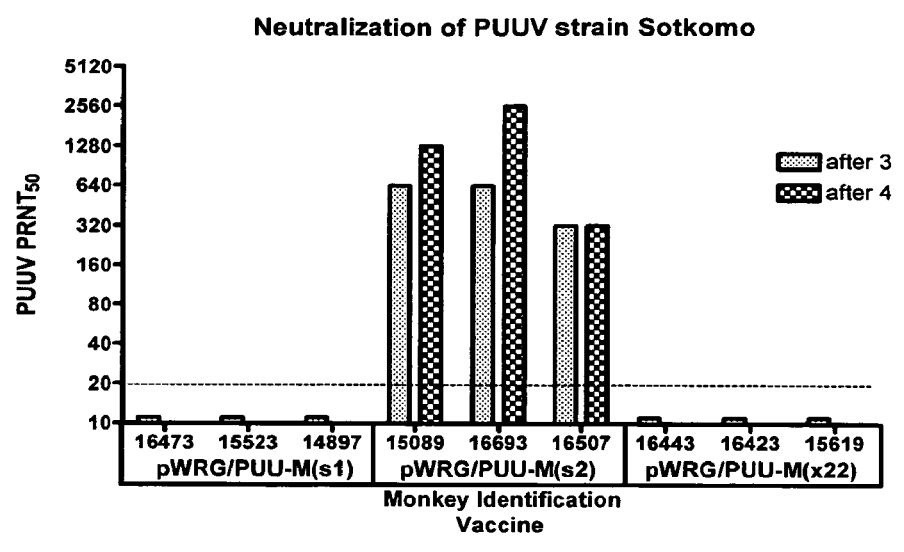

The results are shown in FIG. 4. Potent neutralizing antibody responses were produced in the three nonhuman primates vaccinated with pWRG/PUU-M(s2). The nonhuman primates vaccinated with either pWRG/PUU-M(s1) or pWRG/PUU-M-(x22) did not develop neutralizing antibodies. Thus, the pWRG/PUU-M(s2) PUUV DNA vaccine does elicit a neutralizing antibody response that not only neutralizes a prototype Russian strain, but also the prototype Scandinavian strain of PUUV.

In summary, the inventor has successfully constructed a molecule that, when transfected into mammalian cells, results in the expression of proteins that mimic the Gn and Gc surface glycoproteins of PUUV. When this molecule (e.g., as a DNA vaccine) is introduced into the cells of a vaccinee, the vaccinee produces a neutralizing antibody response against PUUV. Neutralizing antibody responses are sufficient to confer protection against hantaviruses. Thus, pWRG/PUU-M (s2), and derivatives thereof, represent a candidate vaccine for the prevention of HFRS caused by PUUV. Moreover, this plasmid, and derivatives thereof, can be used to generate anti-PUUV immunotherapeutics and diagnostic antibodies in animals.

Other Details of Embodiments of the Invention

One embodiment of the invention encompasses DNA vaccines. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

In order to achieve the immune response sought, a DNA vaccine construct capable of causing transfected cells of the vaccinated individual to express one or more major viral antigenic determinant is necessary. This can be done by identifying regions of the viral genome which code for viral glycoproteins or capsid components, and joining such coding sequences to promoters capable of expressing the sequences in cells of the vaccinee. Alternatively, the viral genome itself, or parts of the genome, can be used.

The new recombinant DNA vaccine approach that involves vaccination with naked DNA expressing individual Puumala virus genome segment cDNAs. Naked DNA vaccination involves delivery of plasmid DNA constructs with a gene(s) of interest into the tissue of the vaccinee (reviewed in Robinson and Torres, 1997, *Semin. Immunol.* 9, 271-283; and Gregoriadis, 1998, *Pharm. Res.* 15, 661-670). DNA vaccination mimics the de novo antigen production and MHC class I-restricted antigen presentation obtainable with live vaccines, without the risks of pathogenic infection. Also, this DNA vaccine approach allows delivery to mucosal tissues which may aid in conferring resistance to viral introduction since entry of the virus may be through mucosal tissues.

The gene(s) of interest, in our case, a synthetic Puumala virus M gene having the sequence identified below as SEQ ID NO:1, is controlled by a mammalian or virus promoter (e.g., the cytomegalovirus immediate early promoter followed by intron A) that facilitates expression of the naked DNA gene product(s) within the vaccinee's cells. It is preferred even to use pWRG/PUU-M(s2) as the DNA vaccine plasmid. This intracellular expression can elicit both humoral and cell-mediated immune responses (Robinson and Torres, 1997, supra; and Gregoriadis, 1998, supra). Methods of DNA delivery include needle inoculation, oral or pulmonary delivery, and inoculation by particle bombardment (i.e., gene gun) and electroporation.

In one aspect of the invention, the DNA vaccine is delivered by coating a small carrier particle with the DNA vaccine and delivering the DNA-coated particle into an animal's epidermal tissue via particle bombardment. This method may be adapted for delivery to either epidermal or mucosal tissue, or delivery into peripheral blood cells, and thus may be used to induce humoral, cell-mediated, and secretory immune responses in the vaccinated individual.

The DNA vaccine according to the present invention is inherently safe, is not painful to administer, and should not result in adverse side effects to the vaccinated individual. In addition, the invention does not require growth or use of Puumala virus, we describe the elicitation of protective immunity to Puumala virus by DNA vaccines. The DNA can be delivered by injection into the tissue of the recipient, oral or pulmonary delivery, inoculation by particle bombardment (i.e., gene gun), and electroporation. Any of these methods can be used to deliver DNA as long as the DNA is expressed and the desired antigen is made in the cell. Two methods are exemplified in this application, both shown to be successful in eliciting a protective immune response in the vaccinee.

To deliver DNA vaccines by particle bombardment, the inventor chose to use the PowderJect-XR™ gene gun device described in WO 95/19799, 27 July 1995 and also a hand-held disposable gene gun (ND10 device) produced by PowderMed. Other instruments are available and known to people in the art. This instrument, which delivers DNA-coated gold beads directly into epidermal cells by high-velocity particle bombardment, was shown to more efficiently induce both humoral and cell-mediated immune responses, with smaller quantities of DNA, than inoculation of the same DNAs by other parenteral routes (Eisenbraun, M. et al., 1993, *DNA Cell. Biol.* 12: 791; Fynan, E. F. et al., 1993, *Proc. Natl. Acad. Sci. USA* 90: 11478; Haynes, J. R. et al., 1994, *AIDS Res. Hum. Retroviruses* 10: Suppl. 2:S43; Pertmer, T. M. et al., 1995, *Vaccine* 13: 1427). Epidermal inoculation of the DNA candidate vaccines also offers the advantages of gene expression in an immunologically active tissue that is generally exfoliated within 15 to 30 days, and which is an important natural focus of viral replication after tick-bite (Bos, J. D., 1997, *Clin. Exp. Immunol.* 107 Suppl. 1:3; Labuda, M. et al., 1996, *Virology* 219:357; Rambukkana, A. et al., 1995, *Lab. Invest.* 73:521; Stingl, G., 1993, *Recent Results Cancer Res.* 128:45).

The vaccine can also be combined with reagents which increase the antigenicity of the vaccine, or reduce its side effects.

The technique of accelerated particles gene delivery or particle bombardment is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platinum, tungsten, etc.) or inert plastic (polystyrene, polypropylene, polycarbonate, etc.). Preferably, the particle is made of gold, platinum or tungsten. Most preferably, the particle is made of gold. Suitably, the particle is spherical and has a diameter of 0.5 to 5 microns, preferably 1 to 3 microns.

The DNA sequence containing the desired gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 0.5 and 30 micrograms of DNA per milligram of gold bead spheres. A preferable ratio of DNA to gold is 0.5-5.0 ug of DNA per milligram of gold.

A sample procedure begins with gamma irradiated (preferably about 30 kGy) tefzel tubing. The gold is weighed out into a microfuge tube, spermidine (free base) at about 0.05 M is added and mixed, and then the DNA is added. A 10% CaCl solution is incubated along with the DNA for about 10 minutes to provide a fine calcium precipitate. The precipitate carries the DNA with it onto the beads. The tubes are microfuged and the pellet resuspended and washed in 100% ethanol and the final product resuspended in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderMed, preferably a hand-held, disposable device designated ND10. Other relevant technology is described in WO 95/19799. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350-400 psi). The particles are entrained in the gas stream and are delivered with sufficient force toward the target tissue to enter the cells of the tissue. Further details are available in the published apparatus application. In particular, PowderMed has developed a hand-held, disposable particle mediated epidermal delivery device that involves the preparation of DNA-coated gold powder and the loading of the powder into a cassette that is contained within the device. A discharge of pressurized helium from a canister contained within the device disrupts membranes on the cassette and the DNA-coated gold powder is propelled out of the device and into the epidermis of the vaccinee.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a DNA vaccine capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

A DNA vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response.

To obtain additional effectiveness from this technique, it may also be desirable that the genes be delivered to a mucosal tissue surface, in order to ensure that mucosal, humoral and cellular immune responses are produced in the vaccinated individual. There are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of DNA, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the amount of DNA per particle. This precise control over the level and form of antigen production may allow for control over the nature of the resultant immune response.

The term transfected is used herein to refer to cells which have incorporated the delivered foreign DNA vaccine, whichever delivery technique is used.

It is herein disclosed that when inducing cellular, humoral, and protective immune responses after DNA vaccination the preferred target cells are epidermal cells, rather than cells of deeper skin layers such as the dermis. Epidermal cells are preferred recipients of DNA vaccines because they are the most accessible cells of the body and may, therefore, be immunized non-invasively. Secondly, in addition to eliciting a humoral immune response, DNA immunized epidermal cells also elicit a cytotoxic immune response that is stronger than that generated in sub-epidermal cells. Delivery to epidermis also has the advantages of being less invasive and delivering to cells which are ultimately sloughed by the body.

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it reduces the severity of the disease symptoms. It is preferred that the immunization method be at least 20% effective in preventing morbidity or death in an immunized population after challenge with Puumala virus. More preferably, the vaccination method is 50% or more effective, and most preferably 70-100% effective, in preventing morbidity or death in an immunized population.

Hamsters have been used extensively as the laboratory model of choice for assessment of protective immune responses to hantaviruses.

Generally, the DNA vaccine administered may be in an amount of about 1-8 ug of DNA per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine for eliciting an immune response against one or more viruses, may be given in a single dose schedule, or preferably a multiple dose schedule in which a primary course of vaccination may be with 1-8 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

Electroporation is another method of delivery of the vaccine. Well-known methods of electroporation are effective for this DNA vaccine. For instance, Hooper et al. (February 2008), describes methods useful for this. (Hooper et al., "Immune Serum Produced by DNA Vaccination Protects Hamsters against Lethal Respiratory Challenge with Andes Virus", J. Virology, February 2008, Vol. 82, No. 3, pp. 1332-1338). In addition, mammals such as rabbits can be vaccinated by muscle electroporation with a DNA vaccine plasmid such as pWRG/PUU-M(s2) to rapidly generate sera containing high-titer PUUV neutralizing antibodies. Sera can be collected and tested for neutralizing antibodies by PRNT.

In another embodiment, the present invention relates to polyclonal antibodies from vaccinees receiving the DNA vaccines described above. A composition comprising the polyclonal antibodies can be used as a prophylactic or therapeutic effective in preventing onset of Puumala virus infection after exposure to it, and/or in treating Puumala virus disease. For example, the composition of the present invention is composed of polyclonal antiserum from a population of animals/humans vaccinated with a DNA vaccine comprised of a plasmid expressing the above-described synthetic Puumala virus M gene. The polyclonal serum would contain neutralizing antibodies against Puumala virus. Unlike conventional polyclonal immune serum products, the process used to make this invention (DNA vaccination of primate antibody producing vaccinees) does not involve live virus and does not require the identification of patients who have survived Puumala virus disease.

In one embodiment of this method, the invention contemplates a method to treat or prevent Puumala virus infection by administering a therapeutically or prophylactically effective amount of serum of the present invention or a mixture of antibodies of the present invention to a subject in need of such treatment.

The term "antibody" is art-recognized terminology and is intended to include molecules or active fragments of molecules that bind to known antigens. These active fragments can be derived from an antibody of the present invention by a number of techniques. For further description of general techniques for the isolation of active fragments of antibodies, see for example, Khaw, B. A. et al. *J. Nucl. Med.* 23:1011-1019 (1982). The term "antibody" also includes bispecific and chimeric antibodies and antibodies in nonmammalian species.

The polyclonal antibodies described herein are characterized in that the antibody binds to the appropriate immunogen, i.e. G1 and G2, as measured by assays such as ELISA, immunoprecipitation, or immunofluorescence. Also, the antibodies must neutralize Puumala virus as measured by plaque reduction neutralization test (PRNT). Any antibody retaining these characteristics is related to the present invention. The polyclonal antibody may be concentrated, irradiated, and tested for a capacity to neutralize Puumala virus. Serum lots with sufficiently high neutralizing antibody titers, i.e., high enough to give a detectable response in the recipient after transfer can be pooled. The product can then be lyophilized for storage and reconstituted for use.

The invention further covers passive vaccines for treating or preventing Puumala virus infections comprising a therapeutically or prophylactically effective amount of the antibodies of the present invention which protect against Puumala virus disease in combination with a pharmaceutically acceptable carrier or excipient. As described in greater detail above, the present inventor has found that serum from a vaccinee immunized with a DNA vaccine comprising the Puumala virus M segment described above contains antibodies able to neutralize Puumala virus and display in vitro and in vivo Puumala virus neutralization properties.

Given these results, polyclonal antibodies according to the present invention are suitable both as therapeutic and prophylactic agents for treating or preventing *hantavirus* infection or disease in susceptible *hantavirus*-exposed subjects. Subjects include rodents such as mice or guinea pigs, birds or avian, and mammals, including humans.

In general, this will comprise administering a therapeutically or prophylactically effective amount of polyclonal antibodies of the present invention to a subject after possible exposure to Puumala virus or to a subject exhibiting Puumala virus symptoms. Any active form of the antibodies can be administered. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the antibodies does not result in clearance of the antibodies before virus can be controlled, and the induced immune response to the antibodies in the subject does not induce "serum sickness" in the subject.

Treatment of individuals having Puumala infection may comprise the administration of a therapeutically effective amount of anti-*hantavirus* antibodies of the present invention. The antibodies can be provided in a kit as described below. In providing a patient with antibodies, or fragments thereof, capable of binding to Puumala virus, or an antibody capable of protecting against Puumala virus in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

The antibodies capable of protecting against Puumala virus are intended to be provided to recipient subjects in an amount sufficient to effect a reduction in the Puumala virus infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provide a method for diagnosis of Puumala virus infection by assaying for the presence of Puumala virus in a sample using the antibodies of the present invention. The method includes contacting the sample with polyclonal antibodies of the present invention which bind Puumala virus antigens, allowing the antibody to bind to the Puumala virus antigen(s) to form an immunological complex, detecting the formation of the immunological complex and correlating the presence or absence of the immunological complex with the presence or absence of *hantavirus* antigen in the sample. The sample can be biological, environmental or a food sample.

The language "detecting the formation of the immunological complex" is intended to include discovery of the presence or absence of Puumala virus antigen in a sample. The presence or absence of Puumala virus antigen can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988 555-612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a Puumala virus vaccinee and the polyclonal antibodies of the present invention, are allowed to compete for binding of the antigen. The amount of polyclonal antibody bound is then measured, and a determination is made as to whether the serum contains anti Puumala virus antigen antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1-31), and Schurs, A. H. W. M., et al. 1977 (*Clin. Chim Acta* 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

The present invention also provides novel immunoprobes and test kits for detection of Puumala virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to Puumala virus to form an immunological complex and detecting the formation of the immunological complex such that presence or absence of the immunological complex correlates with presence or absence of Puumala virus. The kit includes a container holding one or more polyclonal antibodies of the present invention which binds a Puumala virus antigen and instructions for using the antibody for the purpose of binding to *hantavirus* antigen to form an immunological complex and detecting the formation of the immunological complex such that the presence or absence of the immunological complex correlates with presence or absence of Puumala virus in the sample. Examples of containers include multiwell plates which allow simultaneous detection of Puumala virus in multiple samples.

References
1. Hooper J W, Custer D M, Thompson E, Schmaljohn C S. DNA vaccination with the *hantaan virus* m gene protects hamsters against three of four HFRS hantaviruses and elicits a high-titer neutralizing antibody response in rhesus monkeys. *J Virol* 2001; 75(18): 8469-8477.
2. Fuller D H, Loudon P, Schmaljohn C. Preclinical and clinical progress of particle-mediated DNA vaccines for infectious diseases. Methods 2006:40:86-97.
3. Custer D M, Thompson E, Schmaljohn C S, et al. Active and passive vaccination against *hantavirus* pulmonary syndrome with Andes virus M genome segment-based DNA vaccine. *J Virol* 2003; 77(18):9894-9905.
4. Hooper J W, Ferro A M, and Wahl-Jensen V. Immune Serum Produced by DNA Vaccination Protects Hamsters Against Lethal Respiratory Challenge with Andes Virus. *Journal of Virology* 2008; (November 21; Epub ahead of print).
5. Hooper J W, Kamrud K I, Elgh F, et al. DNA vaccination with *hantavirus* M segment elicits neutralizing antibodies and protects against Seoul virus infection. *Virology* 1999; 255:269-278.
6. Hooper J W, Custer D M, Smith J., and Wahl-Jensen W. Hantaan/Andes virus DNA vaccine elicits a broadly cross-reactive neutralizing antibody response in nonhuman primates. *Virology* 2006; 347:208-216.
7. Condon C, Watkins S C, Celluzzi C M, et al. DNA-based immunization by in vivo transfection of dendritic cells. *Nat Med* 1996; 10:1122-1128.
8. Barry M A, Johnston S A. Biological features of genetic immunization. *Vaccine* 1997; 15:788-791.

9. Yoshida A, Nagata T, Uchijima M, et al. Advantage of gene gun-mediated over intramuscular inoculation of plasmid DNA vaccine in reproducible induction of specific immune responses. *Vaccine* 2000; 18:1725-1729.
10. Steele K E, Stabler K, VanderZanden L. Cutaneous DNA vaccination against Ebola virus by particle bombardment: histopathology and alteration of CD3-positive dendritic epidermal cells. *Vet Path* 2001; 38:203-215.
11. Monteiro-Riviere N A, Riviere J. The pig as a model for cutaneous pharmacology and toxicology research. In: Tumbleson M E, Schook L B (eds). *Advances in Swine in Biomedical Research*, Vol. 2, New York, Plenum Press, 1996, pp. 425-458.
12. Draize J H, Woodward G, Calvery H O. Methods for the study of irritation and toxicity of substances applied topically to the skin and mucous membranes. *J Pharmacol Exp Ther* 1944; 82,377-390.
13. Klinman D M, Sechler J M G, Conover J, et al. Contribution of cells at the site of DNA vaccination to the generation of antigen-specific immunity and memory. *J Immunol* 1998; 160: 2388-2392.
14. Gurunathan S, Klinman D, Seder R. DNA vaccines. 2000 *Ann Rev Immunol* 2000; 7-74.
15. McElroy A K, Smith J M, Hooper J W, Schmaljohn C S. Andes virus M genome segment is not sufficient to confer the virulence associated with Andes virus in Syrian hamsters. Virology 2004; 326(1):130-139.
16. Charles River Laboratories—Arkansas Division. Assessment of the Local Skin Reactivity and Systemic Toxicity of Hantaan Virus DNA Vaccine pWRG/HTN-M(x) following PowderJect® Delivery to Syrian Hamster Skin. Final Study Report for Protocol Number JTA00001. 2005.

The contents of all cited references (including literature references, issued patents, published patent applications, and co-pending patent applications) cited throughout this application are hereby expressly incorporated by reference.

What is claimed is:

1. A passive vaccine against Puumala virus infection comprising a composition comprising polyclonal antibodies obtained from a population of vaccines vaccinated with a Puumala virus DNA vaccine comprised of a plasmid expressing SEQ ID NO:1.

2. The passive vaccine of claim 1, wherein the plasmid is pWRG/PUU-M(s2).

3. The passive vaccine of claim 1, which is effective against the strains of Puumala virus selected from the group consisting of strains Sotkamo, K27 and P360.

4. The passive vaccine of claim 1, wherein the plasmid comprises:

(i) a vector, and (ii) the DNA fragment comprising the nucleic acid sequence set forth in SEQ ID NO:1, operably linked to a promoter sequence.

5. The passive vaccine of claim 4, wherein the plasmid further comprises a promoter functional in a mammal.

6. The passive vaccine of claim 4, wherein the vector is an expression vector.

7. The passive vaccine of claim 6, wherein the vector is an adenovirus or alphavirus replicon or vesicular stomatitis virus.

* * * * *

SEQUENCE LISTING

```
<160> NUMBER OF SEQ ID NOS: 5

<210> SEQ ID NO 1
<211> LENGTH: 3447
<212> TYPE: DNA
<213> ORGANISM: Puumala virus
<220> FEATURE:
<223> OTHER INFORMATION: Description of Sequence: Synthetic
      polynucleotide

<400> SEQUENCE: 1
atgggcgagc tgtcccctgt gtgcctgtac ctgctgctgc agggcctgct gctgtgtaac        60
accggagccg ccaggaacct gaacgagctg aagatggagt gcccccacac catcagactg       120
ggccagggcc tggtggtggg cagcgtggag ctgcccagcc tgcccatcca gcaggtggag       180
accctgaagc tggagagcag ctgtaacttc gacctgcaca ccagcacagc cggccagcag       240
agcttcacca agtggacctg ggagatcaag ggcgacctgg ccgagaacac ccaggccagc       300
agcaccagct tccagaccaa gagcagcgag gtgaacctga gaggcctgtg cctgatcccc       360
acactggtgg tggagaccgc cgccagaatg agaaagacca tcgcctgcta cgacctgagc       420
tgtaaccaga ccgtgtgtca gcctaccgtg tacctgatgg gccctatcca gacctgtatc       480
accaccaaga gctgcctgct gtccctgggc gatcagagaa tccaggtgaa ctacgagaaa       540
acctactgtg tgagcggcca gctggtggag ggcatctgct tcaaccccat ccacaccatg       600
gccctgagcc agcctagcca cacctacgac atcatgacca tgatggtgag atgctttctg       660
gtgatcaaga aggtgaccag cggcgacagc atgaagatcg agaagaactt cgagaccctg       720
gtgcagaaga tggctgtac cgccaacaac ttccagggct actacatctg cctgatcggc       780
agcagcagcg agcccctgta cgtgcccgcc ctggacgact acagaagcgc cgaggtgctg       840
tccagaatgg ccttcgcccc ccacggcgag gaccacgaca tcgagaaaaa cgccgtgtcc       900
gccatgagaa tcgccggcaa ggtgaccggc aaggccccca gcaccgagtc cagcgacacc       960
gtgcagggca tcgccttcag cggcagcccc ctgtacacct ccaccggcgt gctgaccagc      1020
aaggacgacc ccgtgtacat ctgggccct ggcatcatca tggagggcaa ccacagcatc       1080
tgtgagaaga aaccctgcc cctgacctgg accggcttca tcagcctgcc cggcgagatc       1140
gagaaaacca cccagtgtac cgtgttctgt acctggccg gacctggcgc cgactgtgag       1200
gcctacagcg agaccggcat cttcaacatc agcagcccca cctgcctgat caaccgggtg      1260
```

```
cagagggttca gaggcagcga gcagcagatc aagtttgtgt gccagcgggt ggacatggac    1320
atcaccgtgt actgtaacgg catgaagaag gtgatcctga ccaagacact ggtgatcggc    1380
cagtgtatct acaccttcac cagcatcttc tccctgatcc ccggcgtggc ccacagcctg    1440
gccgtggagc tgtgtgtgcc cggcctgcac ggctgggcca ccatgctgct gctgctgacc    1500
ttctgcttcg gctgggtgct gatccctacc atcaccatga tcctgctgaa gatcctgatc    1560
gccttcgcct acctgtgctc caagtacaac accgacagca gttcagaat cctgatcgag     1620 aaagtgaagc gggagtacca gaaaaccatg gcagcatgg tgtgtgaagt gtgccagtac     1680
gagtgtgaga ccgccaagga gctggagtcc cacagaaaga gctgctccat cggcagctgc    1740
ccctactgcc tgaaccccag cgaggccacc acctccgccc tgcaggccca cttcaaagtg    1800
tgtaagctga ccagccggtt ccaggagaac ctgaggaagt ccctgaccgt gtacgagccc    1860
atgcagggct gctacagaac cctgagcctg ttccggtaca ggagccggtt ctttgtgggc    1920
ctggtgtggt gtgtgctgct ggtgctggag ctgattgtgt gggccgccag cgccgagacc    1980
cagaacctga atgccggctg gaccgacacc gcccacggca cggcatcat ccccatgaaa     2040 accgacctgg agctggactt cagcctgcct agcagcgcct cctacaccta caggcggcag    2100
ctgcagaatc ctgccaacga gcaggagaag atccccttcc acctgcagct gtccaagcag    2160
gtgatccacg ccgagattca gcctgggc cactggatgg acgccacctt caacctgaaa     2220
accgccttcc actgctacgg cagctgtgag aagtacgcct accttggca gaccgccggc     2280 tgcttcatcg agaaggacta cgagtacgag accggctggg gctgtaatcc tcctgattgc    2340
cccggagtgg gcaccggctg tactgcatgt ggcgtgtacc tggacaagct gaagtctgtg    2400
ggcaaggtgt tcaagatcgt gtccctgagg tacacccgga agtgtgtat ccagctgggc     2460 accgagcaga cctgtaagac cgtggacagc aacgattgcc tgatcacaac cagcgtgaaa    2520
gtgtgtctga tcggcaccat cagcaagttc cagcccagcg ataccctgct gtttctgggc    2580
cccctgcagc agggcggcct gatcttcaag cagtggtgta ccaccacctg ccagttcggc    2640
gatcccggcg atatcatgag cacccccacc ggcatgaagt gccctgagct gaacggcagc    2700
ttccggaaga agtgtgcctt cgccaccacc cctgtgtgtc agttcgacgg caacaccatc    2760
agcggctaca gcggatgat cgccaccaag acagcttcc agtccttcaa cgtgaccgag      2820
ccccacatca gcaccagcgc cctggagtgg atcgatcccg acagcagcct gagggaccac    2880
atcaacgtga tcgtgtccag ggacctgagc ttcaggacc tgagcgagac cccctgccag     2940
atcgacctgg ccaccgccag catcgatggc ctgggggca gcggagtggg cttcaacctg     3000
gtgtgtacag tgagcctgac cgagtgtagc gccttcctga ccagcatcaa agcctgtgac    3060
gccgccatgt gttacggcag caccaccgcc aacctggtga ggcagaa caccatccac       3120 attgtgggca aggcggcca cagcggcagc aagtttatgt gctgccacga caccaagtgt    3180
agcagcaccg cctggtggc cgctgccccc cacctggaca gagtgaccgg ctacaaccag    3240
gccgacagcg acaagatttt cgacgacgga gcccctgagt gtggcatgag ttgctggttc    3300
aagaagagcg gcgagtggat tctgggcgtg ctgaacggga attggatggt ggtggccgtg    3360
ctggtcgtgc tgctgatcct gagcatcctg ctgttcaccc tgtgctgccc taggagaccc    3420
agctaccgga aggagcacaa gccctga                                        3447
```

<210> SEQ ID NO 2
<211> LENGTH: 1148
<212> TYPE: PRT
<213> ORGANISM: Puumala virus
<220> FEATURE:
<223> OTHER INFORMATION: Description of sequence: Synthetic polypeptide

<400> SEQUENCE: 2

```
Met Gly Glu Leu Ser Pro Val Cys Leu Tyr Leu Leu Leu Gln Gly Leu
 1               5                  10                  15

Leu Leu Cys Asn Thr Gly Ala Ala Arg Asn Leu Asn Glu Leu Lys Met
             20                  25                  30

Glu Cys Pro His Thr Ile Arg Leu Gly Gln Gly Leu Val Val Gly Ser
         35                  40                  45

Val Glu Leu Pro Ser Leu Pro Ile Gln Gln Val Glu Thr Leu Lys Leu
 50                  55                  60

Glu Ser Ser Cys Asn Phe Asp Leu His Thr Ser Thr Ala Gly Gln Gln
 65                  70                  75                  80

Ser Phe Thr Lys Trp Thr Trp Glu Ile Lys Gly Asp Leu Ala Glu Asn
             85                  90                  95

Thr Gln Ala Ser Ser Thr Ser Phe Gln Thr Lys Ser Ser Glu Val Asn
        100                 105                 110

Leu Arg Gly Leu Cys Leu Ile Pro Thr Leu Val Val Glu Thr Ala Ala
        115                 120                 125

Arg Met Arg Lys Thr Ile Ala Cys Tyr Asp Leu Ser Cys Asn Gln Thr
130                 135                 140

Val Cys Gln Pro Thr Val Tyr Leu Met Gly Pro Ile Thr Cys Ile
145                 150                 155                 160

Thr Thr Lys Ser Cys Leu Leu Ser Leu Gly Asp Gln Arg Ile Gln Val
                165                 170                 175

Asn Tyr Glu Lys Thr Tyr Cys Val Ser Gly Gln Leu Val Glu Gly Ile
            180                 185                 190

Cys Phe Asn Pro Ile His Thr Met Ala Leu Ser Gln Pro Ser His Thr
        195                 200                 205

Tyr Asp Ile Met Thr Met Met Val Arg Cys Phe Leu Val Ile Lys Lys
210                 215                 220

Val Thr Ser Gly Asp Ser Met Lys Ile Glu Lys Asn Phe Glu Thr Leu
225                 230                 235                 240

Val Gln Lys Asn Gly Cys Thr Ala Asn Asn Phe Gln Gly Tyr Tyr Ile
                245                 250                 255

Cys Leu Ile Gly Ser Ser Ser Glu Pro Leu Tyr Val Pro Ala Leu Asp
            260                 265                 270

Asp Tyr Arg Ser Ala Glu Val Leu Ser Arg Met Ala Phe Ala Pro His
        275                 280                 285

Gly Glu Asp His Asp Ile Glu Lys Asn Ala Val Ser Ala Met Arg Ile
        290                 295                 300

Ala Gly Lys Val Thr Gly Lys Ala Pro Ser Thr Glu Ser Ser Asp Thr
305                 310                 315                 320

Val Gln Gly Ile Ala Phe Ser Gly Ser Pro Leu Tyr Thr Ser Thr Gly
                325                 330                 335

Val Leu Thr Ser Lys Asp Asp Pro Val Tyr Ile Trp Ala Pro Gly Ile
            340                 345                 350

Ile Met Glu Gly Asn His Ser Ile Cys Glu Lys Lys Thr Leu Pro Leu
        355                 360                 365

Thr Trp Thr Gly Phe Ile Ser Leu Pro Gly Glu Ile Glu Lys Thr Thr
370                 375                 380
```

-continued

```
Gln Cys Thr Val Phe Cys Thr Leu Ala Gly Pro Gly Ala Asp Cys Glu
385                 390                 395                 400

Ala Tyr Ser Glu Thr Gly Ile Phe Asn Ile Ser Ser Pro Thr Cys Leu
            405                 410                 415

Ile Asn Arg Val Gln Arg Phe Arg Gly Ser Glu Gln Gln Ile Lys Phe
        420                 425                 430

Val Cys Gln Arg Val Asp Met Asp Ile Thr Val Tyr Cys Asn Gly Met
    435                 440                 445

Lys Lys Val Ile Leu Thr Lys Thr Leu Val Ile Gly Gln Cys Ile Tyr
450                 455                 460

Thr Phe Thr Ser Ile Phe Ser Leu Ile Pro Gly Val Ala His Ser Leu
465                 470                 475                 480

Ala Val Glu Leu Cys Val Pro Gly Leu His Gly Trp Ala Thr Met Leu
            485                 490                 495

Leu Leu Leu Thr Phe Cys Phe Gly Trp Val Leu Ile Pro Thr Ile Thr
                500                 505                 510

Met Ile Leu Leu Lys Ile Leu Ile Ala Phe Ala Tyr Leu Cys Ser Lys
        515                 520                 525

Tyr Asn Thr Asp Ser Lys Phe Arg Ile Leu Ile Glu Lys Val Lys Arg
530                 535                 540

Glu Tyr Gln Lys Thr Met Gly Ser Met Val Cys Glu Val Cys Gln Tyr
545                 550                 555                 560

Glu Cys Glu Thr Ala Lys Glu Leu Glu Ser His Arg Lys Ser Cys Ser
            565                 570                 575

Ile Gly Ser Cys Pro Tyr Cys Leu Asn Pro Ser Glu Ala Thr Thr Ser
                580                 585                 590

Ala Leu Gln Ala His Phe Lys Val Cys Lys Leu Thr Ser Arg Phe Gln
        595                 600                 605

Glu Asn Leu Arg Lys Ser Leu Thr Val Tyr Glu Pro Met Gln Gly Cys
610                 615                 620

Tyr Arg Thr Leu Ser Leu Phe Arg Tyr Arg Ser Arg Phe Val Gly
625                 630                 635                 640

Leu Val Trp Cys Val Leu Leu Val Leu Glu Leu Ile Val Trp Ala Ala
            645                 650                 655

Ser Ala Glu Thr Gln Asn Leu Asn Ala Gly Trp Thr Asp Thr Ala His
                660                 665                 670

Gly Ser Gly Ile Ile Pro Met Lys Thr Asp Leu Glu Leu Asp Phe Ser
        675                 680                 685

Leu Pro Ser Ser Ala Ser Tyr Thr Tyr Arg Arg Gln Leu Gln Asn Pro
690                 695                 700

Ala Asn Glu Gln Glu Lys Ile Pro Phe His Leu Gln Leu Ser Lys Gln
705                 710                 715                 720

Val Ile His Ala Glu Ile Gln His Leu Gly His Trp Met Asp Ala Thr
            725                 730                 735

Phe Asn Leu Lys Thr Ala Phe His Cys Tyr Gly Ser Cys Glu Lys Tyr
                740                 745                 750

Ala Tyr Pro Trp Gln Thr Ala Gly Cys Phe Ile Glu Lys Asp Tyr Glu
        755                 760                 765

Tyr Glu Thr Gly Trp Gly Cys Asn Pro Pro Asp Cys Pro Gly Val Gly
770                 775                 780

Thr Gly Cys Thr Ala Cys Gly Val Tyr Leu Asp Lys Leu Lys Ser Val
785                 790                 795                 800
```

```
Gly Lys Val Phe Lys Ile Val Ser Leu Arg Tyr Thr Arg Lys Val Cys
            805                 810                 815

Ile Gln Leu Gly Thr Glu Gln Thr Cys Lys Thr Val Asp Ser Asn Asp
        820                 825                 830

Cys Leu Ile Thr Thr Ser Val Lys Val Cys Leu Ile Gly Thr Ile Ser
    835                 840                 845

Lys Phe Gln Pro Ser Asp Thr Leu Leu Phe Leu Gly Pro Leu Gln Gln
850                 855                 860

Gly Gly Leu Ile Phe Lys Gln Trp Cys Thr Thr Thr Cys Gln Phe Gly
865                 870                 875                 880

Asp Pro Gly Asp Ile Met Ser Thr Pro Thr Gly Met Lys Cys Pro Glu
            885                 890                 895

Leu Asn Gly Ser Phe Arg Lys Lys Cys Ala Phe Ala Thr Thr Pro Val
        900                 905                 910

Cys Gln Phe Asp Gly Asn Thr Ile Ser Gly Tyr Lys Arg Met Ile Ala
    915                 920                 925

Thr Lys Asp Ser Phe Gln Ser Phe Asn Val Thr Glu Pro His Ile Ser
930                 935                 940

Thr Ser Ala Leu Glu Trp Ile Asp Pro Asp Ser Ser Leu Arg Asp His
945                 950                 955                 960

Ile Asn Val Ile Val Ser Arg Asp Leu Ser Phe Gln Asp Leu Ser Glu
            965                 970                 975

Thr Pro Cys Gln Ile Asp Leu Ala Thr Ala Ser Ile Asp Gly Ala Trp
        980                 985                 990

Gly Ser Gly Val Gly Phe Asn Leu Val Cys Thr Val Ser Leu Thr Glu
    995                 1000                1005

Cys Ser Ala Phe Leu Thr Ser Ile Lys Ala Cys Asp Ala Ala Met Cys
   1010                1015                1020

Tyr Gly Ser Thr Thr Ala Asn Leu Val Arg Gly Gln Asn Thr Ile His
1025                1030                1035                1040

Ile Val Gly Lys Gly Gly His Ser Gly Ser Lys Phe Met Cys Cys His
            1045                1050                1055

Asp Thr Lys Cys Ser Ser Thr Gly Leu Val Ala Ala Ala Pro His Leu
        1060                1065                1070

Asp Arg Val Thr Gly Tyr Asn Gln Ala Asp Ser Asp Lys Ile Phe Asp
    1075                1080                1085

Asp Gly Ala Pro Glu Cys Gly Met Ser Cys Trp Phe Lys Lys Ser Gly
1090                1095                1100

Glu Trp Ile Leu Gly Val Leu Asn Gly Asn Trp Met Val Ala Val
1105                1110                1115                1120

Leu Val Val Leu Leu Ile Leu Ser Ile Leu Leu Phe Thr Leu Cys Cys
            1125                1130                1135

Pro Arg Arg Pro Ser Tyr Arg Lys Glu His Lys Pro
        1140                1145

<210> SEQ ID NO 3
<211> LENGTH: 7924
<212> TYPE: DNA
<213> ORGANISM: Puumala virus
<220> FEATURE:
<223> OTHER INFORMATION: Description of Sequence: Synthetic
      polynucleotide
```

<400> SEQUENCE: 3

```
gggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt tgctttgcca cggaacggtc tgcgttgtcg     180
ggaagatgcg tgatctgatc cttcaactca gcaaaagttc gatttattca acaaagccgc     240
cgtcccgtca agtcagcgta atgctctgcc agtgttacaa ccaattaacc aattctgatt     300
agaaaaactc atcgagcatc aaatgaaact gcaatttatt catatcagga ttatcaatac     360
catattttg  aaaaagccgt ttctgtaatg aaggagaaaa ctcaccgagg cagttccata     420
ggatggcaag atcctggtat cggtctgcga ttccgactcg tccaacatca atacaaccta     480
ttaatttccc ctcgtcaaaa ataaggttat caagtgagaa atcaccatga gtgacgactg     540
aatccggtga gaatggcaaa agcttatgca tttctttcca gacttgttca acaggccagc     600
cattacgctc gtcatcaaaa tcactcgcat caaccaaacc gttattcatt cgtgattgcg     660
cctgagcgag acgaaatacg cgatcgctgt taaaaggaca attacaaaca ggaatcgaat     720
gcaaccggcg caggaacact gccagcgcat caacaatatt ttcacctgaa tcaggatatt     780
cttctaatac ctggaatgct gtttt cccgg ggatcgcagt ggtgagtaac catgcatcat     840
caggagtacg gataaaatgc ttgatggtcg aagaggcat  aaattccgtc agccagttta     900
gtctgaccat ctcatctgta acatcattgg caacgctacc tttgccatgt ttcagaaaca     960
actctggcgc atcgggcttc ccatacaatc gatagattgt cgcacctgat tgcccgacat    1020
tatcgcgagc ccatttatac ccatataaat cagcatccat gttggaattt aatcgcggcc    1080
tcgagcaaga cgtttcccgt tgaatatggc tcataacacc ccttgtatta ctgtttatgt    1140
aagcagacag ttttattgtt catgatgata tattttatc  ttgtgcaatg taacatcaga    1200
gattttgaga cacaacgtgg ctttcccccc ccccccggca tgcctgcagg tcgacaatat    1260
tggctattgg ccattgcata cgttgtatct atatcataat atgtacattt atattggctc    1320
atgtccaata tgaccgccat gttgacattg attattgact agttattaat agtaatcaat    1380
tacggggtca ttagttcata gcccatatat ggagttccgc gttacataac ttacggtaaa    1440
tggcccgcct ggctgaccgc ccaacgaccc ccgcccattg acgtcaataa tgacgtatgt    1500
tcccatagta acgccaatag ggactttcca ttgacgtcaa tgggtggagt atttacggta    1560
aactgcccac ttggcagtac atcaagtgta tcatatgcca agtccgcccc ctattgacgt    1620
caatgacggt aaatggcccg cctggcatta tgcccagtac atgaccttac gggactttcc    1680
tacttggcag tacatctacg tattagtcat cgctattacc atggtgatgc ggttttggca    1740
gtacaccaat gggcgtggat agcggtttga ctcacgggga tttccaagtc tccaccccat    1800
tgacgtcaat gggagtttgt tttggcacca aaatcaacgg gactttccaa aatgtcgtaa    1860
taaccccgcc ccgttgacgc aaatgggcgg taggcgtgta cggtgggagg tctatataag    1920
cagagctcgt ttagtgaacc gtcagatcgc ctggagacgc catccacgct gttttgacct    1980
ccatagaaga caccgggacc gatccagcct ccgcggccgg gaacggtgca ttggaacgcg    2040
gattccccgt gccaagagtg acgtaagtac cgcctataga ctctataggc acacccttt     2100
ggctcttatg catgctatac tgttttt ggc ttggggccta tacacccccg cttccttatg    2160
ctataggtga tggtatagct tagcctatag gtgtgggtta ttgaccatta ttgaccactc    2220
ccctattggt gacgatactt tccattacta atccataaca tggctctttg ccacaactat    2280
ctctattggc tatatgccaa tactctgtcc ttcagagact gacacggact ctgtattttt    2340
```

| | |
|---|---|
| acaggatggg gtcccattta ttatttacaa attcacatat acaacaacgc cgtcccccgt | 2400 |
| gcccgcagtt tttattaaac atagcgtggg atctccacgc gaatctcggg tacgtgttcc | 2460 |
| ggacatgggc tcttctccgg tagcggcgga gcttccacat ccgagccctg gtcccatgcc | 2520 |
| tccagcggct catggtcgct cggcagctcc ttgctcctaa cagtggaggc cagacttagg | 2580 |
| cacagcacaa tgcccaccac caccagtgtg ccgcacaagg ccgtggcggt agggtatgtg | 2640 |
| tctgaaaatg agctcggaga ttgggctcgc accgctgacg cagatggaag acttaaggca | 2700 |
| gcggcagaag aagatgcagg cagctgagtt gttgtattct gataagagtc agaggtaact | 2760 |
| cccgttgcgg tgctgttaac ggtggagggc agtgtagtct gagcagtact cgttgctgcc | 2820 |
| gcgcgcgcca ccagacataa tagctgacag actaacagac tgttcctttc catgggtctt | 2880 |
| ttctgcagtc accgtccaag cttgcggccg cggatctgca ggaattcggc acgagagtag | 2940 |
| tagactccgc aagaaacagc aaacacagat aaatatgggc gagctgtccc ctgtgtgcct | 3000 |
| gtacctgctg ctgcagggcc tgctgctgtg taacaccgga gccgccagga acctgaacga | 3060 |
| gctgaagatg gagtgccccc acaccatcag actgggccag ggcctggtgg tgggcagcgt | 3120 |
| ggagctgccc agcctgccca tccagcaggt ggagaccctg aagctggaga gcagctgtaa | 3180 |
| cttcgacctg cacaccagca cagccggcca gcagagcttc accaagtgga cctgggagat | 3240 |
| caagggcgac ctggccgaga cacccaggc cagcagcacc agcttccaga ccaagagcag | 3300 |
| cgaggtgaac ctgagaggcc tgtgcctgat ccccacactg gtggtggaga ccgccgccag | 3360 |
| aatgagaaag accatcgcct gctacgacct gagctgtaac cagaccgtgt gtcagcctac | 3420 |
| cgtgtacctg atgggcccta tccagacctg tatcaccacc aagagctgcc tgctgtccct | 3480 |
| gggcgatcag agaatccagg tgaactacga gaaaacctac tgtgtgagcg ccagctggt | 3540 |
| ggagggcatc tgcttcaacc ccatccacac catggccctg agccagccta gccacaccta | 3600 |
| cgacatcatg accatgatgg tgagatgctt tctggtgatc aagaaggtga ccagcggcga | 3660 |
| cagcatgaag atcgagaaga acttcgagac cctggtgcag aagaatggct gtaccgccaa | 3720 |
| caacttccag ggctactaca tctgcctgat cggcagcagc agcgagcccc tgtacgtgcc | 3780 |
| cgccctggac gactacagaa gcgccgaggt gctgtccaga atggccttcg ccccccacgg | 3840 |
| cgaggaccac gacatcgaga aaaacgccgt gtccgccatg agaatcgccg gcaaggtgac | 3900 |
| cggcaaggcc cccagcaccg agtccagcga caccgtgcag ggcatcgcct tcagcggcag | 3960 |
| ccccctgtac acctccaccg gcgtgctgac cagcaaggac gaccccgtgt acatctgggc | 4020 |
| ccctggcatc atcatggagg gcaaccacag catctgtgag aagaaaaccc tgcccctgac | 4080 |
| ctggaccggc ttcatcagcc tgcccggcga gatcgagaaa accacccagt gtaccgtgtt | 4140 |
| ctgtaccctg gccggacctg gcgccgactg tgaggcctac agcgagaccg gcatcttcaa | 4200 |
| catcagcagc cccacctgcc tgatcaaccg ggtgcagagg ttcagaggca gcgagcagca | 4260 |
| gatcaagttt gtgtgccagc gggtggacat ggacatcacc gtgtactgta cggcatgaa | 4320 |
| gaaggtgatc ctgaccaaga cactggtgat cggccagtgt atctacacct tcaccagcat | 4380 |
| cttctccctg atccccggcg tggcccacag cctggccgtg gagctgtgtg tgcccggcct | 4440 |
| gcacggctgg gccaccatgc tgctgctgct gaccttctgc ttcggctggg tgctgatccc | 4500 |
| taccatcacc atgatcctgc tgaagatcct gatcgccttc gcctacctgt gctccaagta | 4560 |
| caacaccgac agcaagttca gaatcctgat cgagaaagtg aagcgggagt accagaaaac | 4620 |
| catgggcagc atggtgtgtg aagtgtgcca gtacgagtgt gagaccgcca aggagctgga | 4680 |
| gtcccacaga aagagctgct ccatcggcag ctgcccctac tgcctgaacc ccagcgaggc | 4740 |

```
caccacctcc gccctgcagg cccacttcaa agtgtgtaag ctgaccagcc ggttccagga      4800
gaacctgagg aagtccctga ccgtgtacga gcccatgcag ggctgctaca gaaccctgag      4860
cctgttccgg tacaggagcc ggttctttgt gggcctggtg tggtgtgtgc tgctggtgct      4920
ggagctgatt gtgtgggccg ccagcgccga gacccagaac ctgaatgccg gctggaccga      4980
caccgcccac ggcagcggca tcatccccat gaaaaccgac ctggagctgg acttcagcct      5040
gcctagcagc gcctcctaca cctacaggcg gcagctgcag aatcctgcca acgagcagga      5100
gaagatcccc ttccacctgc agctgtccaa gcaggtgatc cacgccgaga ttcagcacct      5160
gggccactgg atggacgcca ccttcaacct gaaaaccgcc ttccactgct acggcagctg      5220
tgagaagtac gcctacccct tggcagaccgc cggctgcttc atcgagaagg actacgagta      5280
cgagaccggc tggggctgta atcctcctga ttgccccgga gtgggcaccg gctgtactgc      5340
atgtggcgtg tacctggaca agctgaagtc tgtgggcaag gtgttcaaga tcgtgtccct      5400
gaggtacacc cggaaagtgt gtatccagct gggcaccgag cagacctgta agaccgtgga      5460
cagcaacgat tgcctgatca aaccagcgt gaaagtgtgt ctgatcggca ccatcagcaa      5520
gttccagccc agcgataccc tgctgttcct gggcccctg cagcagggcg gcctgatctt      5580
caagcagtgg tgtaccacca cctgccagtt cggcgatccc ggcgatatca tgagcacccc      5640
caccggcatg aagtgccctg agctgaacgg cagcttccgg aagaagtgtg ccttcgccac      5700 caccctgtg tgtcagttcg acggcaacac catcagcggc tacaagcgga tgatcgccac      5760
caaggacagc ttccagtcct tcaacgtgac cgagccccac atcagcacca gcgccctgga      5820
gtggatcgat cccgacagca gcctgaggga ccacatcaac gtgatcgtgt ccagggacct      5880
gagcttccag gacctgagcg agaccccctg ccagatcgac ctggccaccg ccagcatcga      5940
tggcgcctgg ggcagcggag tgggcttcaa cctggtgtgt acagtgagcc tgaccgagtg      6000
tagcgccttc ctgaccagca tcaaagcctg tgacgccgcc atgtgttacg gcagcaccac      6060
cgccaacctg gtgagaggcc agaacaccat ccacattgtg ggcaaaggcg ccacagcgg      6120 cagcaagttt atgtgctgcc acgacaccaa gtgtagcagc accggcctgg tggccgctgc      6180
cccccacctg gacagagtga ccggctacaa ccaggccgac agcgacaaga ttttcgacga      6240
cggagcccct gagtgtggca tgagttgctg gttcaagaag agcggcgagt ggattctggg      6300
cgtgctgaac gggaattgga tggtggtggc cgtgctggtc gtgctgctga tcctgagcat      6360
cctgctgttc accctgtgct gccctaggag acccagctac cggaaggagc acaagccctg      6420
agttttgctt actaacataa ttattgtatt ctgtttattg acacaattac catatgatta      6480
actgtattcc cccatcttat atcttatata atattcttta tttaatcact atatagaaaa      6540
aaaactagca ctttactaat taaattaccc cataccgatt atgcctggac ttttgttcct      6600
gcggagcata ctactaggat ctacgtatga tcagcctcga ctgtgccttc tagttgccag      6660
ccatctgttg tttgccctc cccgtgcct tccttgaccc tggaaggtgc cactcccact      6720
gtcctttcct aataaaatga ggaaattgca tcgcattgtc tgagtaggtg tcattctatt      6780
ctggggggtg gggtggggca ggacagcaag ggggaggatt gggaagacaa tagcaggcat      6840 gctgggggatg cggtgggctc tatggcttct gaggcggaaa gaaccagctg gggctcgaca      6900
gctcgactct agaattgctt cctcgctcac tgactcgctg cgctcggtcg ttcggctgcg      6960
gcgagcggta tcagctcact caaaggcggt aatacggtta tccacagaat caggggataa      7020
cgcaggaaag aacatgtgag caaaaggcca gcaaaaggcc aggaaccgta aaaaggccgc      7080
gttgctggcg ttttttccata ggctccgccc ccctgacgag catcacaaaa atcgacgctc      7140
```

-continued

```
aagtcagagg tggcgaaacc cgacaggact ataaagatac caggcgtttc ccccctggaag    7200 ctccctcgtg cgctctcctg ttccgaccct gccgcttacc ggatacctgt ccgcctttct    7260
cccttcggga agcgtggcgc tttctcatag ctcacgctgt aggtatctca gttcggtgta    7320
ggtcgttcgc tccaagctgg gctgtgtgca cgaaccccccc gttcagcccg accgctgcgc    7380
cttatccggt aactatcgtc ttgagtccaa cccggtaaga cacgacttat cgccactggc    7440
agcagccact ggtaacagga ttagcagagc gaggtatgta ggcggtgcta cagagttctt    7500
gaagtggtgg cctaactacg gctacactag aagaacagta tttggtatct gcgctctgct    7560
gaagccagtt accttcggaa aaagagttgg tagctcttga tccggcaaac aaaccaccgc    7620
tggtagcggt ggttttttg tttgcaagca gcagattacg cgcagaaaaa aaggatctca    7680
agaagatcct ttgatctttt ctacggggtc tgacgctcag tggaacgaaa actcacgtta    7740
agggattttg gtcatgagat tatcaaaaag gatcttcacc tagatccttt taaattaaaa    7800
atgaagtttt aaatcaatct aaagtatata tgagtaaact tggtctgaca gttaccaatg    7860
cttaatcagt gaggcaccta tctcagcgat ctgtctattt cgttcatcca tagttgcctg    7920
actc                                                                 7924
```

<210> SEQ ID NO 4
<211> LENGTH: 3447
<212> TYPE: DNA
<213> ORGANISM: Puumala virus
<220> FEATURE:
<223> OTHER INFORMATION: Description of Sequence: Synthetic
    polynucleotide
<220> FEATURE:
<221> NAME/KEY: CDS
<222> LOCATION: (1)..(3444)

<400> SEQUENCE: 4

```
atg gga gaa ctt agt cca gtt tgt ctg tat ctg ctt ctc cag ggt cta        48
Met Gly Glu Leu Ser Pro Val Cys Leu Tyr Leu Leu Leu Gln Gly Leu
 1               5                  10                  15 tta cta tgt aat aca ggg gct gcc aga aac ctt aat gag ctt aaa atg        96
Leu Leu Cys Asn Thr Gly Ala Ala Arg Asn Leu Asn Glu Leu Lys Met
             20                  25                  30 gaa tgt cca cat act att aga tta ggg cag ggt ctt gtt gtg ggt tca       144
Glu Cys Pro His Thr Ile Arg Leu Gly Gln Gly Leu Val Val Gly Ser
         35                  40                  45 gta gaa ttg cca tct ctt cca ata cag cag gtc gag aca cta aag ctg       192
Val Glu Leu Pro Ser Leu Pro Ile Gln Gln Val Glu Thr Leu Lys Leu
     50                  55                  60 gag agt tct tgt aat ttt gat cta cat acc agt aca gca gga caa caa       240
Glu Ser Ser Cys Asn Phe Asp Leu His Thr Ser Thr Ala Gly Gln Gln
 65                  70                  75                  80 tca ttc aca aaa tgg aca tgg gaa att aaa ggt gat ctt gca gag aac       288
Ser Phe Thr Lys Trp Thr Trp Glu Ile Lys Gly Asp Leu Ala Glu Asn
                 85                  90                  95 aca cag gca tca tca aca agt ttt caa aca aaa agc agt gaa gtg aat       336
Thr Gln Ala Ser Ser Thr Ser Phe Gln Thr Lys Ser Ser Glu Val Asn
            100                 105                 110 ttg aga gga tta tgt ttg atc cct act tta gtg gtt gaa aca gca gca       384
Leu Arg Gly Leu Cys Leu Ile Pro Thr Leu Val Val Glu Thr Ala Ala
        115                 120                 125 aga atg cga aaa aca ata gca tgt tat gac ctg tca tgc aat caa aca       432
Arg Met Arg Lys Thr Ile Ala Cys Tyr Asp Leu Ser Cys Asn Gln Thr
    130                 135                 140
```

| | | |
|---|---|---|
| gtg tgt cag cct act gtc tat tta atg gga cct atc cag act tgt ata<br>Val Cys Gln Pro Thr Val Tyr Leu Met Gly Pro Ile Gln Thr Cys Ile<br>145                            150                       155                   160 | | 480 |
| aca act aaa agt tgt ctc ttg agt tta ggt gat caa agg att caa gta<br>Thr Thr Lys Ser Cys Leu Leu Ser Leu Gly Asp Gln Arg Ile Gln Val<br>                       165                     170                      175 | | 528 |
| aat tat gaa aaa aca tac tgt gtt tct ggg cag ctt gtt gaa ggt atc<br>Asn Tyr Glu Lys Thr Tyr Cys Val Ser Gly Gln Leu Val Glu Gly Ile<br>                  180                     185                    190 | | 576 |
| tgt ttt aat cca ata cat aca atg gca ctc tct caa cct agt tat aca<br>Cys Phe Asn Pro Ile His Thr Met Ala Leu Ser Gln Pro Ser Tyr Thr<br>             195                     200                    205 | | 624 |
| tat gat ata atg acc atg atg gtt cgc tgt ttc ttg gta ata aag aaa<br>Tyr Asp Ile Met Thr Met Met Val Arg Cys Phe Leu Val Ile Lys Lys<br>210                          215                       220 | | 672 |
| gtg act tct ggt gac agt atg aag att gaa aag aac ttt gag act ctt<br>Val Thr Ser Gly Asp Ser Met Lys Ile Glu Lys Asn Phe Glu Thr Leu<br>225                          230                     235                240 | | 720 |
| gtt caa aaa aat ggc tgc aca gct aat aac ttc caa ggg tat tat atc<br>Val Gln Lys Asn Gly Cys Thr Ala Asn Asn Phe Gln Gly Tyr Tyr Ile<br>                       245                     250                    255 | | 768 |
| tgt ctt ata ggg agt agt tca gag ccc tta tat gtt cca gca tta gat<br>Cys Leu Ile Gly Ser Ser Ser Glu Pro Leu Tyr Val Pro Ala Leu Asp<br>                  260                     265                    270 | | 816 |
| gat tat cgt tca gct gaa gtt ctt tca agg atg gca ttt gca cca cat<br>Asp Tyr Arg Ser Ala Glu Val Leu Ser Arg Met Ala Phe Ala Pro His<br>             275                     280                    285 | | 864 |
| ggt gaa gat cat gat att gag aaa aat gca gtg agt gca atg cgt att<br>Gly Glu Asp His Asp Ile Glu Lys Asn Ala Val Ser Ala Met Arg Ile<br>290                          295                     300 | | 912 |
| gct gga aag gtg aca gga aag gcg cca tca aca gaa tca tca gat aca<br>Ala Gly Lys Val Thr Gly Lys Ala Pro Ser Thr Glu Ser Ser Asp Thr<br>305                          310                     315                320 | | 960 |
| gta cag ggg att gca ttt tca ggt agt cct ctt tat aca tct act ggt<br>Val Gln Gly Ile Ala Phe Ser Gly Ser Pro Leu Tyr Thr Ser Thr Gly<br>                  325                     330                    335 | | 1008 |
| gtc ttg aca tca aaa gat gat cct gtc tac att tgg gct cct gga atc<br>Val Leu Thr Ser Lys Asp Asp Pro Val Tyr Ile Trp Ala Pro Gly Ile<br>             340                     345                    350 | | 1056 |
| ata atg gaa gga aac cat tct att tgt gaa aag aag acc tta ccc ctt<br>Ile Met Glu Gly Asn His Ser Ile Cys Glu Lys Lys Thr Leu Pro Leu<br>                  355                     360                    365 | | 1104 |
| aca tgg act ggt ttt att tca ttg cct gga gag att gaa aaa aca aca<br>Thr Trp Thr Gly Phe Ile Ser Leu Pro Gly Glu Ile Glu Lys Thr Thr<br>370                          375                     380 | | 1152 |
| caa tgt aca gta ttt tgt aca ttg gct gga cca ggt gca gat tgt gaa<br>Gln Cys Thr Val Phe Cys Thr Leu Ala Gly Pro Gly Ala Asp Cys Glu<br>385                          390                     395                400 | | 1200 |
| gct tac tct gaa aca ggc atc ttc aac ata agt tca cct act tgc tta<br>Ala Tyr Ser Glu Thr Gly Ile Phe Asn Ile Ser Ser Pro Thr Cys Leu<br>                  405                     410                    415 | | 1248 |
| ata aat cgt gtc cag aga ttc cgt ggt tca gaa cag caa ata aag ttt<br>Ile Asn Arg Val Gln Arg Phe Arg Gly Ser Glu Gln Gln Ile Lys Phe<br>             420                     425                    430 | | 1296 |
| gtg tgc cag aga gtg gac atg gat atc act gtt tac tgt aat ggg acg<br>Val Cys Gln Arg Val Asp Met Asp Ile Thr Val Tyr Cys Asn Gly Thr<br>             435                     440                    445 | | 1344 |
| aag aaa gtc att ctc acc aag acc cta gtt att gga caa tgc att tat<br>Lys Lys Val Ile Leu Thr Lys Thr Leu Val Ile Gly Gln Cys Ile Tyr<br>450                          455                     460 | | 1392 |

-continued

| | | |
|---|---|---|
| act ttt act agt att ttc tct cta atc cct ggt gtt gca cat tcc ctt<br>Thr Phe Thr Ser Ile Phe Ser Leu Ile Pro Gly Val Ala His Ser Leu<br>465                                   470                            475                         480 | | 1440 |
| gct gtt gaa tta tgt gta cct ggt ctt cat ggt cgg gca act atg cta<br>Ala Val Glu Leu Cys Val Pro Gly Leu His Gly Arg Ala Thr Met Leu<br>485                           490                         495 | | 1488 |
| tta tta cta aca ttt tgt ttt ggc tgg gtc tta ata cca act ata aca<br>Leu Leu Leu Thr Phe Cys Phe Gly Trp Val Leu Ile Pro Thr Ile Thr<br>500                         505                       510 | | 1536 |
| atc ctg cta aag ata ttg att gca ttc gca tac tta tgt tct aaa<br>Met Ile Leu Leu Lys Ile Leu Ile Ala Phe Ala Tyr Leu Cys Ser Lys<br>515                         520                       525 | | 1584 |
| tat aac aca gat tcg aaa ttc agg atc ttg att gag aaa gtg aaa aga<br>Tyr Asn Thr Asp Ser Lys Phe Arg Ile Leu Ile Glu Lys Val Lys Arg<br>530                         535                       540 | | 1632 |
| gag tac cag aaa aca atg ggt tca atg gtt tgt gaa gtg tgt cag tat<br>Glu Tyr Gln Lys Thr Met Gly Ser Met Val Cys Glu Val Cys Gln Tyr<br>545                         550                       555                       560 | | 1680 |
| gaa tgt gag act gca aaa gaa ctg gag tca cat aga aag agt tgt tcc<br>Glu Cys Glu Thr Ala Lys Glu Leu Glu Ser His Arg Lys Ser Cys Ser<br>565                         570                       575 | | 1728 |
| att ggt tca tgc cct tat tgt ctc aat cca tct gag gca aca aca tct<br>Ile Gly Ser Cys Pro Tyr Cys Leu Asn Pro Ser Glu Ala Thr Thr Ser<br>580                         585                       590 | | 1776 |
| gcc ctt cag gct cat ttt aaa gtg tgt aag ctc aca tca cgg ttt cag<br>Ala Leu Gln Ala His Phe Lys Val Cys Lys Leu Thr Ser Arg Phe Gln<br>595                         600                       605 | | 1824 |
| gag aat tta aga aag tca tta acg gta tat gag cct atg caa ggg tgc<br>Glu Asn Leu Arg Lys Ser Leu Thr Val Tyr Glu Pro Met Gln Gly Cys<br>610                         615                       620 | | 1872 |
| tac cgg act tta tcc ctc ttt aga tat agg agt cgg ttc ttt gtg ggt<br>Tyr Arg Thr Leu Ser Leu Phe Arg Tyr Arg Ser Arg Phe Phe Val Gly<br>625                         630                       635                       640 | | 1920 |
| cta gtc tgg tgc gtg tta ttg gtt cta gag tta att gta tgg gct gcc<br>Leu Val Trp Cys Val Leu Leu Val Leu Glu Leu Ile Val Trp Ala Ala<br>645                         650                       655 | | 1968 |
| agt gct gaa aca caa aat tta aat gca ggt tgg aca gac aca gca cat<br>Ser Ala Glu Thr Gln Asn Leu Asn Ala Gly Trp Thr Asp Thr Ala His<br>660                         665                       670 | | 2016 |
| gga tct gga att ata cct atg aaa act gat ctg gaa tta gac ttc tct<br>Gly Ser Gly Ile Ile Pro Met Lys Thr Asp Leu Glu Leu Asp Phe Ser<br>675                         680                       685 | | 2064 |
| ctt ccg tca tca gca agc tat aca tat agg aga cag cta caa aac cca<br>Leu Pro Ser Ser Ala Ser Tyr Thr Tyr Arg Arg Gln Leu Gln Asn Pro<br>690                         695                       700 | | 2112 |
| gca aac gaa caa gag aaa atc cca ttt cat ctg cag tta agc aaa caa<br>Ala Asn Glu Gln Glu Lys Ile Pro Phe His Leu Gln Leu Ser Lys Gln<br>705                         710                       715                       720 | | 2160 |
| gtg att cat gca gag atc cag cat tta ggt cat tgg atg gat gct aca<br>Val Ile His Ala Glu Ile Gln His Leu Gly His Trp Met Asp Ala Thr<br>725                         730                       735 | | 2208 |
| ttt aat ctt aaa act gca ttt cac tgc tat ggc tca tgt gag aag tat<br>Phe Asn Leu Lys Thr Ala Phe His Cys Tyr Gly Ser Cys Glu Lys Tyr<br>740                         745                       750 | | 2256 |
| gct tat cct tgg cag aca gca ggt tgt ttc ata gaa aaa gat tat gaa<br>Ala Tyr Pro Trp Gln Thr Ala Gly Cys Phe Ile Glu Lys Asp Tyr Glu<br>755                         760                       765 | | 2304 |
| tat gag act ggt tgg ggt tgt aat cca cct gat tgc cca ggg gta ggg<br>Tyr Glu Thr Gly Trp Gly Cys Asn Pro Pro Asp Cys Pro Gly Val Gly<br>770                         775                       780 | | 2352 |

```
aca ggc tgt act gct tgt ggg gta tac ctt gat aaa tta aaa tca gtt    2400
Thr Gly Cys Thr Ala Cys Gly Val Tyr Leu Asp Lys Leu Lys Ser Val
785                 790                 795                 800 gga aag gtt ttc aaa att gtg tcc tta aga tac aca agg aaa gta tgc    2448
Gly Lys Val Phe Lys Ile Val Ser Leu Arg Tyr Thr Arg Lys Val Cys
            805                 810                 815 att cag ttg ggc aca gaa caa aca tgt aag act gtt gat agt aat gac    2496
Ile Gln Leu Gly Thr Glu Gln Thr Cys Lys Thr Val Asp Ser Asn Asp
        820                 825                 830 tgt ctc att acc act tca gtt aaa gtg tgc ttg ata ggg acc ata tca    2544
Cys Leu Ile Thr Thr Ser Val Lys Val Cys Leu Ile Gly Thr Ile Ser
    835                 840                 845 aaa ttc caa cca tct gac act ttg cta ttt cta ggt cca cta cag cag    2592
Lys Phe Gln Pro Ser Asp Thr Leu Leu Phe Leu Gly Pro Leu Gln Gln
850                 855                 860 ggt ggt ctg ata ttt aaa caa tgg tgc act aca aca tgc cag ttt ggc    2640
Gly Gly Leu Ile Phe Lys Gln Trp Cys Thr Thr Thr Cys Gln Phe Gly
865                 870                 875                 880 gat ccc ggg gac ata atg agc aca cct aca ggc atg aag tgc cca gaa    2688
Asp Pro Gly Asp Ile Met Ser Thr Pro Thr Gly Met Lys Cys Pro Glu
            885                 890                 895 tta aat ggt tct ttt aga aag aaa tgt gca ttt gca aca act cca gtt    2736
Leu Asn Gly Ser Phe Arg Lys Lys Cys Ala Phe Ala Thr Thr Pro Val
        900                 905                 910 tgc cag ttt gat gga aat aca att tca ggc tat aag agg atg att gcc    2784
Cys Gln Phe Asp Gly Asn Thr Ile Ser Gly Tyr Lys Arg Met Ile Ala
    915                 920                 925 aca aag gat tca ttt caa tct ttc aat gtg aca gaa ccc cat att tct    2832
Thr Lys Asp Ser Phe Gln Ser Phe Asn Val Thr Glu Pro His Ile Ser
930                 935                 940 aca agt gca ctt gaa tgg att gat cct gac agc tca ctt agg gac cat    2880
Thr Ser Ala Leu Glu Trp Ile Asp Pro Asp Ser Ser Leu Arg Asp His
945                 950                 955                 960 att aat gta att gtg agt cgt gat cta tcc ttc cga gac cta agt gaa    2928
Ile Asn Val Ile Val Ser Arg Asp Leu Ser Phe Arg Asp Leu Ser Glu
            965                 970                 975 aca cca tgt caa att gat tta gca aca gcc tct ata gat gga gca tgg    2976
Thr Pro Cys Gln Ile Asp Leu Ala Thr Ala Ser Ile Asp Gly Ala Trp
        980                 985                 990 ggt tca gga gtt ggt ttt aat ctg gtt tgt act gtt agt tta aca gaa    3024
Gly Ser Gly Val Gly Phe Asn Leu Val Cys Thr Val Ser Leu Thr Glu
    995                 1000                1005 tgt tct gca ttt ctg aca tca atc aag gcc tgt gat gct gca atg tgt    3072
Cys Ser Ala Phe Leu Thr Ser Ile Lys Ala Cys Asp Ala Ala Met Cys
    1010                1015                1020 tat ggg tcc acc aca gcc aat cta gtt cga ggg caa aat acc att cat    3120
Tyr Gly Ser Thr Thr Ala Asn Leu Val Arg Gly Gln Asn Thr Ile His
1025                1030                1035                1040 atc gtc ggt aag ggt ggg cat tct ggt tca aaa ttt atg tgt tgt cat    3168
Ile Val Gly Lys Gly Gly His Ser Gly Ser Lys Phe Met Cys Cys His
            1045                1050                1055 gac aca aaa tgt tct agc acc ggt cta gtt gca gct gca cca cac tta    3216
Asp Thr Lys Cys Ser Ser Thr Gly Leu Val Ala Ala Ala Pro His Leu
        1060                1065                1070 gat cgt gtg aca gga tac aat cag gct gat agt gac aaa atc ttt gat    3264
Asp Arg Val Thr Gly Tyr Asn Gln Ala Asp Ser Asp Lys Ile Phe Asp
    1075                1080                1085 gat ggg gca cca gaa tgt ggt atg tta tgt tgg ttt aaa aaa tca ggt    3312
Asp Gly Ala Pro Glu Cys Gly Met Leu Cys Trp Phe Lys Lys Ser Gly
    1090                1095                1100
```

```
gaa tgg att ctt ggg gtt ttg aac ggg aat tgg atg gtt gtt gct gta      3360
Glu Trp Ile Leu Gly Val Leu Asn Gly Asn Trp Met Val Val Ala Val
1105               1110                1115                1120 ctg gta gta tta ctg atc ttg tcc ata ctc tta ttc aca tta tgt tgt      3408
Leu Val Val Leu Leu Ile Leu Ser Ile Leu Leu Phe Thr Leu Cys Cys
                1125                1130                1135 cct cgt aga cct agt tac agg aaa gaa cat aag ccc taa                  3447
Pro Arg Arg Pro Ser Tyr Arg Lys Glu His Lys Pro
                1140                1145

<210> SEQ ID NO 5
<211> LENGTH: 1148
<212> TYPE: PRT
<213> ORGANISM: Puumala virus
<220> FEATURE:
<223> OTHER INFORMATION: Description of Sequence: Synthetic polypeptide

<400> SEQUENCE: 5

Met Gly Glu Leu Ser Pro Val Cys Leu Tyr Leu Leu Leu Gln Gly Leu
 1               5                  10                  15

Leu Leu Cys Asn Thr Gly Ala Ala Arg Asn Leu Asn Glu Leu Lys Met
            20                  25                  30

Glu Cys Pro His Thr Ile Arg Leu Gly Gln Gly Leu Val Val Gly Ser
        35                  40                  45

Val Glu Leu Pro Ser Leu Pro Ile Gln Gln Val Glu Thr Leu Lys Leu
    50                  55                  60

Glu Ser Ser Cys Asn Phe Asp Leu His Thr Ser Thr Ala Gly Gln Gln
65                  70                  75                  80

Ser Phe Thr Lys Trp Thr Trp Glu Ile Lys Gly Asp Leu Ala Glu Asn
                85                  90                  95

Thr Gln Ala Ser Ser Thr Ser Phe Gln Thr Lys Ser Ser Glu Val Asn
            100                 105                 110

Leu Arg Gly Leu Cys Leu Ile Pro Thr Leu Val Val Glu Thr Ala Ala
        115                 120                 125

Arg Met Arg Lys Thr Ile Ala Cys Tyr Asp Leu Ser Cys Asn Gln Thr
    130                 135                 140

Val Cys Gln Pro Thr Val Tyr Leu Met Gly Pro Ile Gln Thr Cys Ile
145                 150                 155                 160

Thr Thr Lys Ser Cys Leu Leu Ser Leu Gly Asp Gln Arg Ile Gln Val
                165                 170                 175

Asn Tyr Glu Lys Thr Tyr Cys Val Ser Gly Gln Leu Val Glu Gly Ile
            180                 185                 190

Cys Phe Asn Pro Ile His Thr Met Ala Leu Ser Gln Pro Ser Tyr Thr
        195                 200                 205

Tyr Asp Ile Met Thr Met Met Val Arg Cys Phe Leu Val Ile Lys Lys
    210                 215                 220

Val Thr Ser Gly Asp Ser Met Lys Ile Glu Lys Asn Phe Glu Thr Leu
225                 230                 235                 240

Val Gln Lys Asn Gly Cys Thr Ala Asn Asn Phe Gln Gly Tyr Tyr Ile
                245                 250                 255

Cys Leu Ile Gly Ser Ser Ser Glu Pro Leu Tyr Val Pro Ala Leu Asp
            260                 265                 270

Asp Tyr Arg Ser Ala Glu Val Leu Ser Arg Met Ala Phe Ala Pro His
        275                 280                 285

Gly Glu Asp His Asp Ile Glu Lys Asn Ala Val Ser Ala Met Arg Ile
    290                 295                 300
```

-continued

```
Ala Gly Lys Val Thr Gly Lys Ala Pro Ser Thr Glu Ser Ser Asp Thr
305                 310                 315                 320

Val Gln Gly Ile Ala Phe Ser Gly Ser Pro Leu Tyr Thr Ser Thr Gly
            325                 330                 335

Val Leu Thr Ser Lys Asp Asp Pro Val Tyr Ile Trp Ala Pro Gly Ile
            340                 345                 350

Ile Met Glu Gly Asn His Ser Ile Cys Glu Lys Lys Thr Leu Pro Leu
            355                 360                 365

Thr Trp Thr Gly Phe Ile Ser Leu Pro Gly Glu Ile Glu Lys Thr Thr
            370                 375                 380

Gln Cys Thr Val Phe Cys Thr Leu Ala Gly Pro Gly Ala Asp Cys Glu
385                 390                 395                 400

Ala Tyr Ser Glu Thr Gly Ile Phe Asn Ile Ser Ser Pro Thr Cys Leu
            405                 410                 415

Ile Asn Arg Val Gln Arg Phe Arg Gly Ser Glu Gln Gln Ile Lys Phe
            420                 425                 430

Val Cys Gln Arg Val Asp Met Asp Ile Thr Val Tyr Cys Asn Gly Thr
            435                 440                 445

Lys Lys Val Ile Leu Thr Lys Thr Leu Val Ile Gly Gln Cys Ile Tyr
450                 455                 460

Thr Phe Thr Ser Ile Phe Ser Leu Ile Pro Gly Val Ala His Ser Leu
465                 470                 475                 480

Ala Val Glu Leu Cys Val Pro Gly Leu His Gly Arg Ala Thr Met Leu
            485                 490                 495

Leu Leu Leu Thr Phe Cys Phe Gly Trp Val Leu Ile Pro Thr Ile Thr
            500                 505                 510

Met Ile Leu Leu Lys Ile Leu Ile Ala Phe Ala Tyr Leu Cys Ser Lys
            515                 520                 525

Tyr Asn Thr Asp Ser Lys Phe Arg Ile Leu Ile Glu Lys Val Lys Arg
530                 535                 540

Glu Tyr Gln Lys Thr Met Gly Ser Met Val Cys Glu Val Cys Gln Tyr
545                 550                 555                 560

Glu Cys Glu Thr Ala Lys Glu Leu Glu Ser His Arg Lys Ser Cys Ser
            565                 570                 575

Ile Gly Ser Cys Pro Tyr Cys Leu Asn Pro Ser Glu Ala Thr Thr Ser
            580                 585                 590

Ala Leu Gln Ala His Phe Lys Val Cys Lys Leu Thr Ser Arg Phe Gln
            595                 600                 605

Glu Asn Leu Arg Lys Ser Leu Thr Val Tyr Glu Pro Met Gln Gly Cys
610                 615                 620

Tyr Arg Thr Leu Ser Leu Phe Arg Tyr Arg Ser Arg Phe Phe Val Gly
625                 630                 635                 640

Leu Val Trp Cys Val Leu Leu Val Leu Glu Leu Ile Val Trp Ala Ala
            645                 650                 655

Ser Ala Glu Thr Gln Asn Leu Asn Ala Gly Trp Thr Asp Thr Ala His
            660                 665                 670

Gly Ser Gly Ile Ile Pro Met Lys Thr Asp Leu Glu Leu Asp Phe Ser
            675                 680                 685

Leu Pro Ser Ser Ala Ser Tyr Thr Tyr Arg Arg Gln Leu Gln Asn Pro
            690                 695                 700

Ala Asn Glu Gln Glu Lys Ile Pro Phe His Leu Gln Leu Ser Lys Gln
705                 710                 715                 720
```

-continued

Val Ile His Ala Glu Ile Gln His Leu Gly His Trp Met Asp Ala Thr
            725                 730                 735

Phe Asn Leu Lys Thr Ala Phe His Cys Tyr Gly Ser Cys Glu Lys Tyr
            740                 745                 750

Ala Tyr Pro Trp Gln Thr Ala Gly Cys Phe Ile Glu Lys Asp Tyr Glu
            755                 760                 765

Tyr Glu Thr Gly Trp Gly Cys Asn Pro Pro Asp Cys Pro Gly Val Gly
            770                 775                 780

Thr Gly Cys Thr Ala Cys Gly Val Tyr Leu Asp Lys Leu Lys Ser Val
785                 790                 795                 800

Gly Lys Val Phe Lys Ile Val Ser Leu Arg Tyr Thr Arg Lys Val Cys
            805                 810                 815

Ile Gln Leu Gly Thr Glu Gln Thr Cys Lys Thr Val Asp Ser Asn Asp
            820                 825                 830

Cys Leu Ile Thr Thr Ser Val Lys Val Cys Leu Ile Gly Thr Ile Ser
            835                 840                 845

Lys Phe Gln Pro Ser Asp Thr Leu Leu Phe Leu Gly Pro Leu Gln Gln
            850                 855                 860

Gly Gly Leu Ile Phe Lys Gln Trp Cys Thr Thr Thr Cys Gln Phe Gly
865                 870                 875                 880

Asp Pro Gly Asp Ile Met Ser Thr Pro Thr Gly Met Lys Cys Pro Glu
            885                 890                 895

Leu Asn Gly Ser Phe Arg Lys Lys Cys Ala Phe Ala Thr Thr Pro Val
            900                 905                 910

Cys Gln Phe Asp Gly Asn Thr Ile Ser Gly Tyr Lys Arg Met Ile Ala
            915                 920                 925

Thr Lys Asp Ser Phe Gln Ser Phe Asn Val Thr Glu Pro His Ile Ser
            930                 935                 940

Thr Ser Ala Leu Glu Trp Ile Asp Pro Asp Ser Ser Leu Arg Asp His
945                 950                 955                 960

Ile Asn Val Ile Val Ser Arg Asp Leu Ser Phe Arg Asp Leu Ser Glu
            965                 970                 975

Thr Pro Cys Gln Ile Asp Leu Ala Thr Ala Ser Ile Asp Gly Ala Trp
            980                 985                 990

Gly Ser Gly Val Gly Phe Asn Leu Val Cys Thr Val Ser Leu Thr Glu
            995                 1000                1005

Cys Ser Ala Phe Leu Thr Ser Ile Lys Ala Cys Asp Ala Ala Met Cys
1010                1015                1020

Tyr Gly Ser Thr Thr Ala Asn Leu Val Arg Gly Gln Asn Thr Ile His
1025                1030                1035                1040

Ile Val Gly Lys Gly Gly His Ser Gly Ser Lys Phe Met Cys Cys His
            1045                1050                1055

Asp Thr Lys Cys Ser Ser Thr Gly Leu Val Ala Ala Ala Pro His Leu
            1060                1065                1070

Asp Arg Val Thr Gly Tyr Asn Gln Ala Asp Ser Asp Lys Ile Phe Asp
            1075                1080                1085

Asp Gly Ala Pro Glu Cys Gly Met Leu Cys Trp Phe Lys Lys Ser Gly
            1090                1095                1100

Glu Trp Ile Leu Gly Val Leu Asn Gly Asn Trp Met Val Val Ala Val
1105                1110                1115                1120

-continued

```
Leu Val Val Leu Leu Ile Leu Ser Ile Leu Leu Phe Thr Leu Cys Cys
            1125            1130            1135

Pro Arg Arg Pro Ser Tyr Arg Lys Glu His Lys Pro
        1140            1145
```